United States Patent [19]

Petersen et al.

[11] Patent Number: 5,202,337
[45] Date of Patent: Apr. 13, 1993

[54] 7-(2,7-DIAZABICYCLO[3.3.0]OCTYL)-3-QUINOLONE-AND-NAPHTHYRIDONE-CARBOXYLIC ACID DERIVATIVES

[75] Inventors: Uwe Petersen; Thomas Schenke, both of Leverkusen; Michael Schriewer, Odenthal; Klaus Grohe, Odenthal; Andreas Krebs, Odenthal; Ingo Haller, Wuppertal; Karl G. Metzger, Wuppertal; Klaus-Dieter Bremm, Wuppertal; Rainer Endermann, Wuppertal; Hans-Joachim Zeiler, Wuppertal, all of Fed. Rep. of Germany

[73] Assignee: Bayer Aktiengesellschaft, Leverkusen, Fed. Rep. of Germany

[21] Appl. No.: 771,700

[22] Filed: Oct. 3, 1991

[30] Foreign Application Priority Data

Oct. 13, 1990 [DE] Fed. Rep. of Germany ....... 4032560

[51] Int. Cl.$^5$ .................... A61K 31/47; C07D 521/00

[52] U.S. Cl. ......................................... 514/312; 544/4; 544/32; 544/64; 544/101; 546/5; 546/89; 546/123; 546/156

[58] Field of Search ..................... 546/156, 5; 514/312

[56] References Cited

FOREIGN PATENT DOCUMENTS

| | | |
|---|---|---|
| 0106489 | 4/1984 | European Pat. Off. . |
| 0172651 | 2/1986 | European Pat. Off. . |
| 0284935 | 10/1988 | European Pat. Off. . |
| 0343524 | 11/1989 | European Pat. Off. . |
| 0350733 | 1/1990 | European Pat. Off. . |

Primary Examiner—C. Warren Ivy
Assistant Examiner—James H. Turnipseed
Attorney, Agent, or Firm—Sprung Horn Kramer & Woods

[57] ABSTRACT

The invention relates to new 7-(2,7-Diazabicyclo[3.3.-0]octyl)-3-quinolone- and -naphthyridonecarboxylic acid derivatives, processes for their preparation, and antibacterial agents and feed additives containing them.

11 Claims, No Drawings

7-(2,7-DIAZABICYCLO[3.3.0]OCTYL)-3-QUINO-LONE-AND-NAPHTHYRIDONE-CARBOXYLIC ACID DERIVATIVES

The invention relates to new 7-(2,7-diazabicyclo[3.3.-0]octyl)-3-quinolone- and -naphthyridonecarboxylic acid derivatives, processes for their preparation, and antibacterial agents and feed additives containing them.

3-Quinolone- and -naphthyridonecarboxylic acids which are substituted in the 7-position by a 2,7-diazabicyclo[3.3.0]octyl ring have already been disclosed in EP-A-0,350,733.

It has now been found that the new 7-(2,7-diazabicyclo[3.3.0]octyl)-3-quinolone- and -naphthyridonecarboxylic acid derivatives of the formula (I)

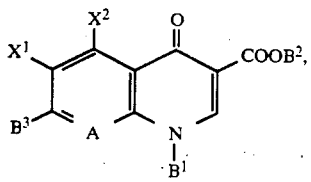

in which
X$^1$ represents halogen,
X$^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or methyl,
B$^1$ represents alkyl having 1 to 4 carbon atoms, alkenyl having 2 to 4 carbon atoms, cycloalkyl having 3 to 6 carbon atoms, 2-hydroxyethyl, 2-fluoroethyl, methoxy, amino, methylamino, ethylamino, dimethylamino, or phenyl which is optionally substituted by 1 or 2 fluorine atoms,
B$^2$ represents hydrogen, alkyl having 1 to 4 carbon atoms or (5-methyl-2-oxo-1,3-dioxol-4-yl)-methyl,
B$^3$ represents a radical of the structure

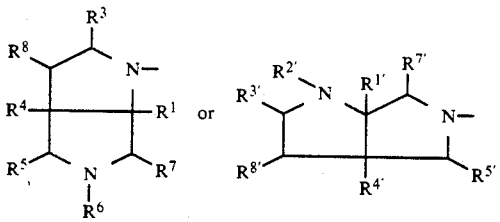

where
R$^1$, R$^3$, R$^4$, R$^5$, R$^7$ and R$^8$ are identical or different and in each case represent hydrogen or methyl which can optionally be substituted by halogen or hydroxyl, or represent C$_1$-C$_2$-alkoxycarbonyl or carboxyl,
R$^4$ and R$^8$ can additionally represent halogen, amino, hydroxyl or methoxy,
R$^6$ represents hydrogen, C$_1$-C$_6$-alkyl, benzyl, C$_6$-C$_{12}$-aryl, C$_1$-C$_3$-alkanoyl, benzoyl or C$_1$-C$_5$-alkoxycarbonyl,
R$^{1'}$, R$^{2'}$, R$^{3'}$, R$^{5'}$, R$^{7'}$ and R$^{8'}$ are identical or different and in each case represent hydrogen or methyl,
R$^{4'}$ represents halogen, amino, hydroxyl, methoxy or methyl which can optionally be substituted by halogen, amino, hydroxyl or methoxy, or represents hydrogen when
R$^{2'}$ and R$^{3'}$ together denote a C$_2$-C$_4$-alkylene bridge or a CH$_2$—S—CH$_2$ bridge which can optionally be monosubstituted or disubstituted by hydroxyl, methoxy, amino or methyl,
A represents N or C—R$^9$, where
R$^9$ represents H, halogen, methyl, cyano, nitro, hydroxyl or methoxy, or, alternatively, together with B$^1$ can form a bridge of the structure

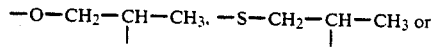

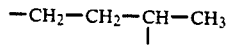

and their hydrates and acid addition salts which can be used in pharmaceutics, as well as the alkali metal salts, alkaline earth metal salts, silver salts and guanidinium salts of the carboxylic acids on which they are based, have a powerful antibacterial action, in particular in the gram-positive sector.

Preferred compounds of the formula (I) are those in which
X$^1$ represents fluorine or chlorine,
X$^2$ represents hydrogen, amino, alkylamino having 1 to 2 carbon atoms, dimethylamino, hydroxyl, methoxy, mercapto, methylthio, fluorine or methyl,
B$^1$ represents alkyl having 1 to 3 carbon atoms, alkenyl having 2 to 3 carbon atoms, cycloalkyl having 3 to 5 carbon atoms, 2-hydroxyethyl, 2-fluoroethyl, methoxy, amino, methylamino, ethylamino, dimethylamino, or phenyl which is optionally substituted by 1 or 2 fluorine atoms,
B$^2$ represents hydrogen, alkyl having 1 to 3 carbon atoms or (5-methyl-2-oxo-1,3-dioxol-4-yl)-methyl
B$^3$ represents a radical of the above-described structure, where
R$^1$, R$^3$, R$^4$, R$^5$, R$^7$ and R$^8$ are identical or different and in each case represent hydrogen or methyl which can optionally be substituted by halogen, or represent C$_1$-C$_3$-alkoxycarbonyl
R$^4$ can additionally represent halogen such as fluorine chlorine or bromine,
R$^6$ represents hydrogen, C$_1$-C$_3$-alkyl, benzyl, phenyl, acetyl, benzoyl or C$_1$-C$_4$-alkoxycarbonyl,
R$^{1'}$, R$^{2'}$, R$^{3'}$, R$^{5'}$, R$^{7'}$ and R$^{8'}$ are identical or different and in each case represent hydrogen or methyl,
R$^{4'}$ represents halogen such as chlorine or bromine, or represents hydrogen when
R$^{2'}$ and R$^{3'}$ together denote a C$_2$-C$_4$-alkylene bridge or a CH$_2$—S—CH$_2$ bridge which can optionally be monosubstituted or disubstituted by hydroxyl or methyl,
A represents N or C—R$^9$, where
R$^9$ represents H, halogen or methoxy, or, alternatively, together with B$^1$ can form a bridge of the structure

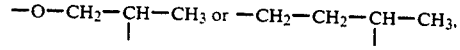

and their hydrates and acid addition salts which can be used in pharmaceutics, as well as the alkali metal salts and alkaline earth metal salts of the carboxylic acids on which they are based.

Particularly preferred compounds of the formula (I) are those in which $X^1$ represents fluorine, $X^2$ represents hydrogen, amino, fluorine or methyl, $B^1$ represents alkyl having 1 to 2 carbon atoms, vinyl, cyclopropyl, 2-hydroxyethyl, 2-fluoroethyl, methoxy, methylamino, 4-fluorophenyl or 2,4-difluorophenyl, $B^2$ represents hydrogen or alkyl having 1 to 2 carbon atoms, $B^3$ represents a radical of the above-described structure, where $R^1$, $R^3$, $R^4$, $R^5$, $R^7$ and $R^8$ are identical or different and in each case represent hydrogen or methyl which can optionally be substituted by fluorine, $R^4$ can additionally represent fluorine, chlorine or bromine, $R^6$ represents hydrogen, methyl, acetyl or $C_1$-$C_4$-alkoxy carbonyl, $R^{1'}$, $R^{2'}$, $R^{3'}$, $R^{5'}$, $R^{7'}$ and $R^{8'}$ are identical or different and in each case represent hydrogen or methyl, $R^{4'}$ represents chlorine or bromine, or represents hydrogen when $R^{2'}$ and $R^{3'}$ together denote a $C_2$-$C_4$-alkylene bridge or a $CH_2$—S—$CH_2$ bridge, each of which can optionally be monosubstituted or disubstituted by hydroxyl or methyl, A represents N or C—$R^9$, where $R^9$ represents H, halogen or methoxy, or, alternatively, together with $B^1$ can form a bridge of the structure

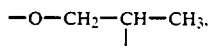

and their hydrates and acid addition salts which can be used in pharmaceutics, as well as the alkali metal salts of the carboxylic acids on which they are based Furthermore, it has been found that the compounds of the formula (I) are obtained when compounds of the formula (II)

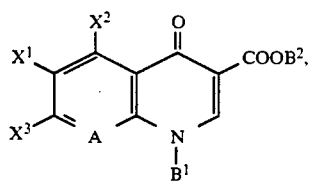

in which

A, $B^1$, $B^2$, $X^1$ and $X^2$ have the abovementioned meaning and $X^3$ represents halogen, in particular fluorine or chlorine, are reacted with compounds of the formula (III)

 (III), in which $B^3$ has the abovementioned meaning, if appropriate in the presence of acid scavengers, and, if appropriate, protective groups contained in $B^3$, are eliminated (method A).

Compounds of the formula (I) according to the invention in which $X^1$, $B^1$, $B^2$, $B^3$ and A have the abovementioned meaning and $X^2$ represents amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, or arylthio, can also be obtained by reacting a compound of the formula (IV)

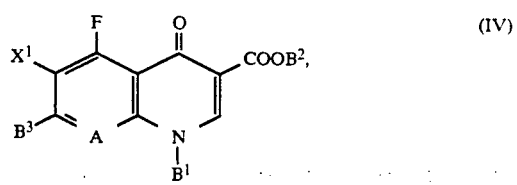

in which $X^1$, $B^1$, $B^2$, $B^3$ and A have the abovementioned meaning, with compounds of the formula (V)

in which $X^2$ has the abovementioned meaning, if appropriate in the presence of acid scavengers (method B).

If, for example, 1-cyclopropyl-6,7,8-trifluoro-1,4-dihydro-4-oxo-3-quinolinecarboxylic acid and 1,4-diazatricyclo[6.2.0.0$^{2.6}$]decane are used as starting substances, the course of the reaction can be illustrated by the following equation:

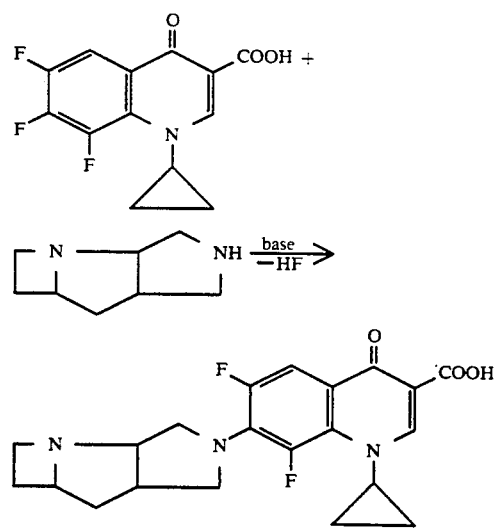

If, for example, 7-chloro-6-fluoro-1-(2,4-difluorophenyl)-1,4-dihydro-4-oxo-1,8-naphthyridine-3-carboxylic acid and 7-tert.-butoxycarbonyl-5-methyl-2,7-diazabicyclo[3.3.0]octane are used as starting substances, the course of the reaction can be illustrated by the following equation:

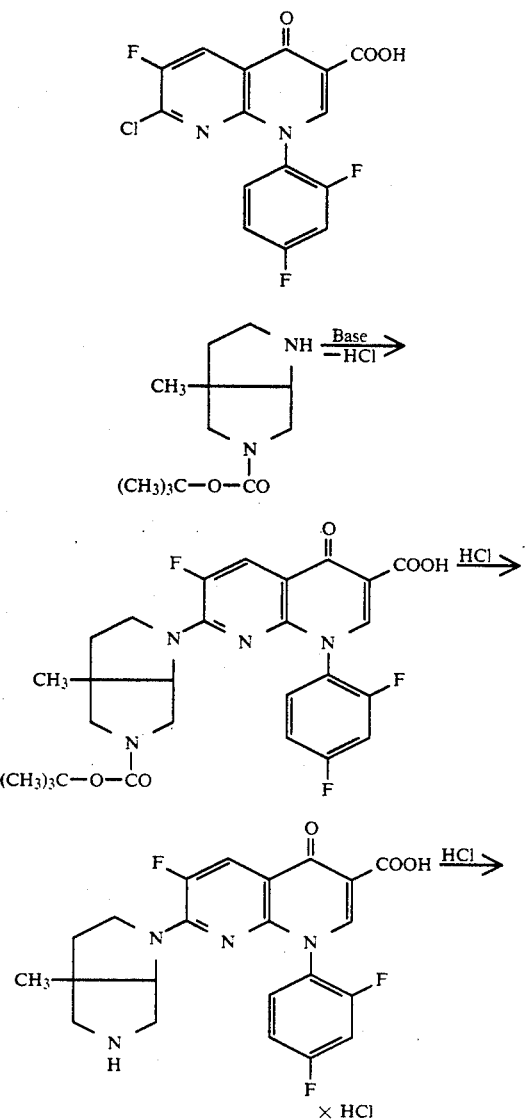

If, for example, 1-cyclopropyl-5,6,8-trifluoro-1,4-dihydro-7-(7-methyl-2,7-diazabicyclo[3.3.0]oct-2-yl)-4-oxo-3-quinolinecarboxylic acid and ammonia are used as starting substances, the course of the reaction can be illustrated by the following equation:

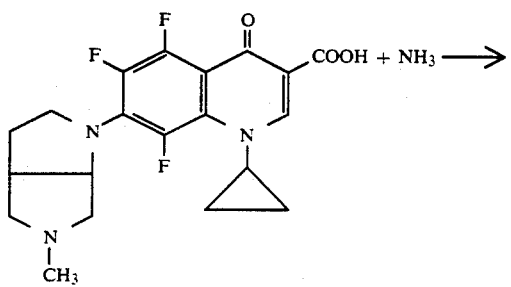

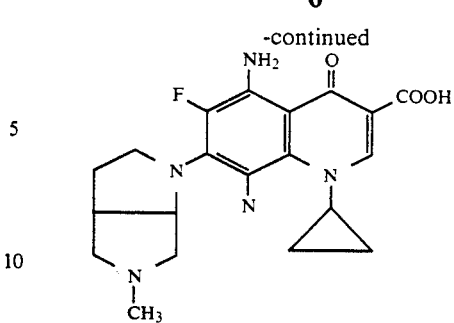

The compounds of the formula (II) which are used as starting substances are known or can be prepared by known methods. The following may be mentioned as examples:

7-chloro-1-cyclopropyl-6-fluoro-1,4-dihydro-4-oxo-3-quinolinecarboxylic acid (DE-A-3,142,854),
1-cyclopropyl-6,7-difluoro-1,4-dihydro-4-oxo-3-quinolinecarboxylic acid (EP-A-113,091),
6-chloro-1-cyclopropyl-7,8-difluoro-1,4-dihydro-4-oxo-3-quinolinecarboxylic acid (DE-A-3,420,743),
8-chloro-1-cyclopropyl-6,7-difluoro-1,4-dihydro-4-oxo-3-quinolinecarboxylic acid (DE-A-3,420,743),
1-cyclopropyl-6,7,8-trifluoro-1,4-dihydro-4-oxo-3-quinolinecarboxylic acid (DE-A-3,318,145),
6,8-dichloro-1-cyclopropyl-7-fluoro-1,4-dihydro-4-oxo-3-quinolinecarboxylic acid (DE-A-3,420,743),
1-cyclopropyl-6,7-difluoro-1,4-dihydro-8-methyl-4-oxo-3-quinolinecarboxylic acid,
1-cyclopropyl-7-chloro-6-fluoro-1,4-dihydro-8-nitro-4-oxo-3-quinolinecarboxylic acid,
6,7-difluoro-1-ethyl-1,4-dihydro-4-oxo-3-quinolinecarboxylic acid,
7-chloro-6-fluoro-1-ethyl-1,4-dihydro-4-oxo-3-quinolinecarboxylic acid,
7-chloro-6-fluoro-1,4-dihydro-1-(2-hydroxyethyl)-4-oxo-3-quinolinecarboxylic acid,
6,7-difluoro-1-(2-fluoroethyl)-1,4-dihydro-4-oxo-3-quinolinecarboxylic acid,
7-chloro-6-fluoro-1,4-dihydro-1-methoxy-4-oxo-3-quinolinecarboxylic acid,
7-chloro-6-fluoro-1,4-dihydro-1-methylamino-4-oxo-3-quinolinecarboxylic acid,
6,7-difluoro-1,4-dihydro-4-oxo-1-phenyl-3-quinolinecarboxylic acid,
7-chloro-1-cyclopropyl-6-fluoro-1,4-dihydro-4-oxo-1,8-naphthyridine-3-carboxylic acid,
6,7-dichloro-1-cyclopropyl-1,4-dihydro-4-oxo-1,8-naphthyridine-3-carboxylic acid,
ethyl 1-cyclopropyl-6,7,8-trifluoro-1,4-dihydro-4-oxo-3-quinolinecarboxylate (EP-A-3,318,145),
9,10-difluoro-2,3-dihydro-3-methyl-7-oxo-7H-pyrido[1,2,3-de][1,4]benzoxazine-6-carboxylic acid (EP-A-47,005),
8,9-difluoro-6,7-dihydro-5-methyl-1-oxo-1H,5H-benzo[i,j]quinolicine-2-carboxylic acid,
7-chloro-6-fluoro-1-phenyl-1,4-dihydro-4-oxo-1,8-naphthyridine-3-carboxylic acid (EP-A-153,580),
7-chloro-6-fluoro-1-(4-fluorophenyl)-1,4-dihydro-4-oxo-1,8-naphthyridine-3-carboxylic acid (EP-A-153,580),
6,7,8-trifluoro-1,4-dihydro-1-methylamino-4-oxo-3-quinolinecarboxylic acid (DE-A-3,409,922),
7-chloro-6-fluoro-1,4-dihydro-8-nitro-4-oxo-1-phenyl-3-quinolinecarboxylic acid, 7-chloro-6-fluoro-1-(4-fluorophenyl)-1,4-dihydro-8-nitro-4-oxo-3-quinolinecarboxylic acid, 6,7-difluoro-1-(4-fluorophenyl)-1,4-dihydro-8-methyl-4-oxo-3-quinolinecarboxylic acid, 6-chloro-7-fluoro-1-(4-fluorophenyl)-1,4-dihydro-4-oxo-3-quinolinecarboxylic acid (EP-A-131,839), 6-chloro-7-fluoro-1-(2,4-difluorophenyl)-1,4-dihydro-4-oxo-3-quinolinecarboxylic acid (EP-A-131,839), 6,7,8-trifluoro-1-(4-fluorophenyl)-1,4-dihydro-4-oxo-3-quinolinecarboxylic acid (EP-A-154,780), 6,7,8-trifluoro-1-(2,4-difluorophenyl)-1,4-dihydro-4-oxo-3-quinolinecarboxylic acid (EP-A-154,780), 6,7,8-trifluoro-1,4-dihydro-4-oxo-1-phenyl-3-quinolinecarboxylic acid (EP-A-154,780), 7-chloro-1-ethyl-6-fluoro-1,4-dihydro-4-oxo-1,8-naphthyridine-3-carboxylic acid, 6,7-difluoro-1,4-dihydro-4-oxo-1-vinyl-3-quinolinecarboxylic acid, 1-cyclopropyl-5,6,7,8-tetrafluoro-1,4-dihydro-4-oxo-3-quinolinecarboxylic acid, 5-amino-1-cyclopropyl-6,7,8-trifluoro-1,4-dihydro-4-oxo-3-quinolinecarboxylic acid, 1-cyclopropyl-6,7,8-trifluoro-1,4-dihydro-5-hydroxy-4-oxo-3-quinolinecarboxylic acid, 1-cyclopropyl-6,7-difluoro-1,4-dihydro-8-methoxy-4-oxo-3-quinolinecarboxylic acid.

The compounds of the formula (III) which are used as starting compounds can be prepared by reacting unsaturated carbonyl compounds of the formula (VI) with amino acid derivatives of the formula (VII) in an intramolecular 1,3-dipolar cyclo addition reaction,

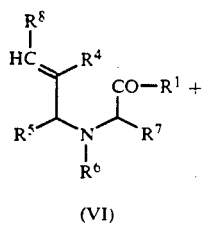

(VI)

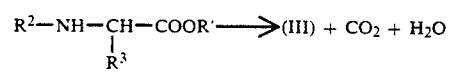

(VII)

where

R' represents H or $C_1$-$C_2$-alkyl and where $R^1$-$R^8$ have the abovementioned meaning. Instead of $R^1$-$R^8$, the meanings given above in the case of $R^{1'}$-$R^{8'}$ may also apply. The substituents $R^2$ or $R^6$, which have a protective-group function, can subsequently be eliminated.

The unsaturated carbonyl compounds of the formula (VI) can be prepared by the following processes:

1. Starting from commercially available aminoacetaldehyde dimethyl acetal, the amino group is acylated, the amide is alkylated with allyl halides in the presence of strong bases, and the acetal is split under acid conditions.

2. If the process starts with a commercially available or known (EP-A-249,530) α-oxoaldehyde monoacetals, the latter can be subjected to reductive amination with allyl amines. After a (protective) group $R^6$ has been introduced by alkylation or acylation, the acetal group is hydrolysed under acid conditions.

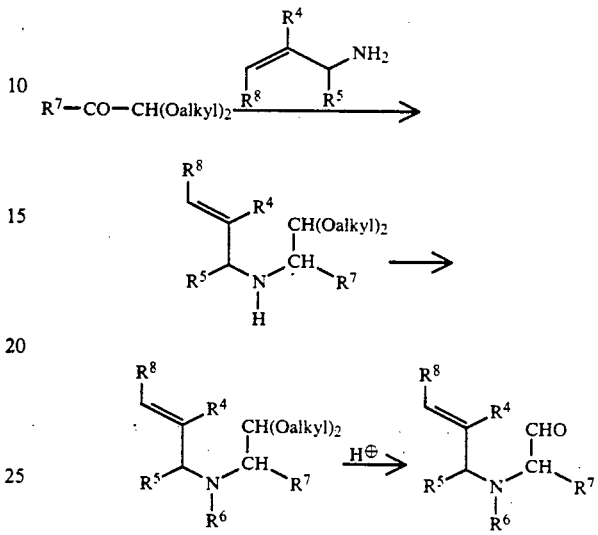

3. Unsaturated aldehydes or ketones can be subjected to reductive amination with aminoacetaldehyde dimethyl acetal. After the group $R^6$ has been introduced by alkylation or acylation, the acetal group can be split under acid conditions.

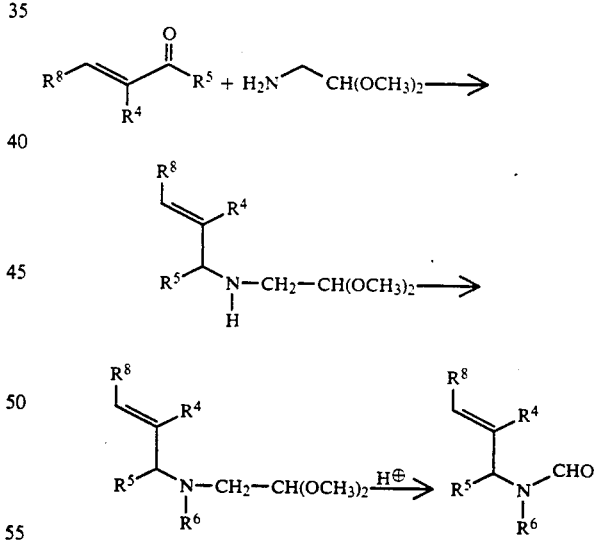

4. N-allylamino alcohols are obtained
   a) by ring opening of epoxides with allylamines (J. pharm. Soc. Japan 73,1330 (1953)),
   b) by alkylation of substituted ethanolamines with allyl halides (J. Am. Chem. Soc. 64, 1692 (1942); 72, 3536 (1950)),
   c) by reductive amination of unsaturated aldehydes or ketones with substituted ethanolamines.

After the $R^6$ group has been introduced by alkylation or acylation, the alcohol function is oxidised with suitable oxidants to give compounds of the formula (VI).

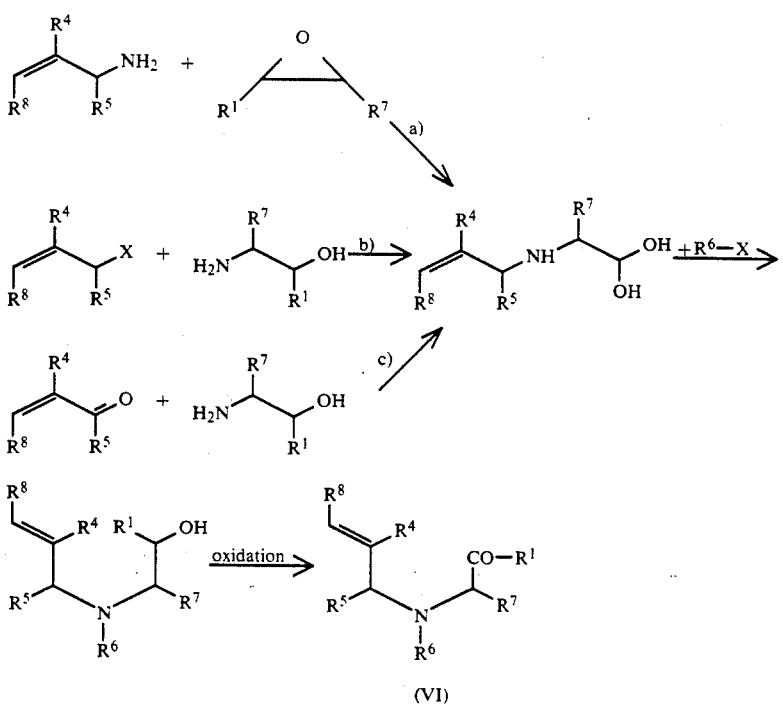

5. Enantiomerically pure educts of the formula (VI) are obtained by alkylation of N-acylated amino acid esters with allyl halides in the presence of strong bases. Using suitable reducing agents, the ester function can be
a) reduced to the aldehyde function or
b) reduced to the alcohol and then oxidised with suitable oxidants to give the aldehyde function.

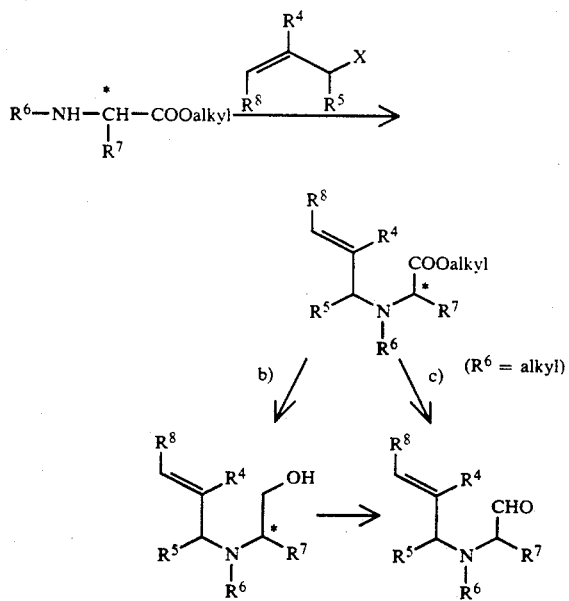

The amino acids of the formula (VII) are known from the literature and mostly commercially available.

The reaction of (VI) with (VII) is carried out in a solvent. Solvents which can be used are hydrocarbons such as benzene, toluene, xylenes or tetralin, ethers such as dioxane, dibutyl ether, dimethoxyethane, diethylene glycol dimethyl ether, diethylene glycol diethyl ether, alcohols such as butanol, pentanol, ethylene glycol, ethylene glycol monomethyl ether and ethylene glycol monoethyl ether, and dipolar aprotic solvents such as dimethylformamide, dimethyl sulphoxide, N-methyl-pyrrolidone and sulpholane. Toluene, xylenes and dimethylformamide are particularly preferred.

The reaction temperature can be varied within a substantial range. In general, the reactions are carried out between 20° C. and 200° C., preferably between 80° C. and 150° C.

The reaction can be carried out under atmospheric pressure, but also under increased pressure. In general, the reaction is carried out under pressures between approximately 1 bar and 100 bar, preferably between approximately 1 bar and 10 bar.

When carrying out the process according to the invention. 0.5 to 6 moles, preferably 0.5 to 2 moles, of amino acid derivative (VII) are employed per mole of unsaturated carbonyl compound (VI).

The reaction can be carried out in such a way that the unsaturated carbonyl compound is added dropwise to a suspension or solution of the amino acid derivative (VII) in one of the solvents mentioned. Alternatively, both components can be initially introduced into a solvent, and the reaction can be carried out in the temperature range mentioned. The reaction water, which is set free during the reaction, can be distilled off together with the solvent as an azeotrope. The course of the reaction can be monitored with ease because of the $CO_2$ development which takes place. Working-up is carried out by removing the solvent and distillation, if appropriate after unreacted amino acid (VII) has been separated off. However, it is also possible to extract the basic products from the organic solvent with an acid, such as, for example, hydrochloric acid, so as to separate off neutral impurities.

In a further step of the process according to the invention, the substituents $R^2$ and $R^6$ can be eliminated in as much as they have the function of protective groups.

Acyl radicals are removed hydrolytically. Suitable substances for hydrolysis are strong acids or strong bases. For acid hydrolysis, aqueous hydrochloric acid, hydrobromic acid or trifluoroacetic acid are preferably used. Basic hydrolysis is carried out using alkali metal hydroxides or alkaline earth metal hydroxides, preferred substances being lithium hydroxide, sodium hydroxide, potassium hydroxide, calcium hydroxide and barium hydroxide. Suitable solvents are water and alcohols, preferred solvents are water, ethanol or mixtures of these solvents. The hydrolysis can be carried out at temperatures between 0° and 200° C., preferably between 20° and 140° C. This process is carried out under pressures of between approximately 1 bar and 100 bar, preferably between approximately 1 bar and 10 bar.

If the radicals $R^2$ or $R^6$ are benzyl radicals, then these radicals can be eliminated hydrogenolytically. Solvents which can be used are water, alcohols, carboxylic acids, alcoholic hydrochloric acid, cyclic ethers or their mixtures. The catalysts used are palladium, both as a sponge and on supports such as active carbon, calcium carbonate or barium sulphate, and palladium hydroxide on active carbon. The process is carried out at temperatures between approximately 0° and 200° C. and hydrogen pressures of from 1 bar to 200 bar.

In as much as the radicals $R^2$ and $R^6$ are acyl radicals, the process moreover also includes their conversion into alkyl radicals by reduction. The reduction can be effected either catalytically or with hydrides or complex hydrides of elements of the third main group. The reduction is preferably effected using diborane, lithium aluminum hydride and sodium borohydride, in the latter case with the addition of Lewis acids such as titanium tetrachloride, aluminium trichloride or boron trifluoride.

The reaction is effected in inert organic solvents such as ethers, for example diethyl ether, dibutyl ether, methyl tert.-butyl ether, tetrahydrofuran, dioxane or ethylene glycol dimethyl ether, or in hydrocarbons such as toluene or xylene. The temperatures can be varied between approximately 0° and 200° C. To achieve high reaction temperatures, the process can be carried out under pressures up to 100 bar.

It is preferred to carry out the reduction process at the reflux temperature of the solvent, using lithium aluminium hydride or sodium borohydride/boron trifluoride etherate in tetrahydrofuran or dioxane.

The reaction of (II) with (III) according to method A of the process according to the invention, in which the compounds (III) can also be employed in the form of their hydrochlorides, is preferably carried out in a diluent such as dimethyl sulphoxide, N,N-dimethylformamide, N-methylpyrrolidone, hexamethylphosphoric triamide, sulpholane, acetonitrile, water, an alcohol such as methanol, ethanol, n-propanol, isopropanol, glycol monomethyl ether or pyridine. It is also possible to use mixtures of these diluents.

Acid binders which can be used are all customary inorganic and organic acid-binding agents. These preferably include the alkali metal hydroxides, alkali metal carbonates, and organic amines and amides. The following may be mentioned individually as being particularly suitable: triethylamine, 1,4-diazabicyclo[2.2.2]octane (DABCO), 1,8-diazabicyclo[5.4.0]undec-7-ene (DBU) or excess amine (III).

The reaction temperatures can be varied within a substantial range. In general, the process is carried out between approximately 20 and 200° C., preferably between 80° and 180° C.

The reaction can be carried out under atmospheric pressure, but also under increased pressure. In general, the process is carried under pressures of between approximately 1 and 100 bar, preferably between 1 and 10 bar.

When carrying out the process according to the invention, 1 to 15 moles, preferably 1 to 6 moles, of the compound (III) are employed per mole of the carboxylic acid (II).

Free hydroxyl groups can be protected during the reaction by a suitable hydroxyl protective group, for example by the tetrahydropyranyl radical, and set free again after the reaction has ended (see J. F. W. McOmie, Protective Groups in Organic Chemistry (1973), page 104).

Free amino functions can be protected during the reaction by a suitable amino protective group, for example by the ethoxycarbonyl or the tert.-butoxycarbonyl radical and set free again after the reaction has ended by treatment with a suitable acid such as hydrochloric acid or trifluoroacetic acid (see Houben-Weyl, Methoden der organischen Chemie, [Methods of Organic Chemistry], Volume E4, page 144 (1983); J. F. W. McOmie, Protective Groups in Organic Chemistry (1973), page 43).

The reaction of (IV) with (V) according to method B of the process according to the invention is preferably carried out in a diluent such as dimethyl sulphoxide, dioxane, N,N-dimethylformamide, N-methylpyrrolidone, hexamethylphosphoric triamide, sulpholane, water, an alcohol such as methanol, ethanol, n-propanol, isopropanol, glycol monomethyl ether or pyridine. Mixtures of these diluents can also be used.

Acid binders which can be used are all customary inorganic and organic acid-binding agents. These preferably include alkali metal hydroxides, alkali metal carbonates, organic amines and amidines. The following may be mentioned individually as being particularly suitable: triethylamine, 1,4-diazabicyclo[2.2.2]octane (DABCO) or 1,8-diazabicyclo[5.4.0]undec-7-ene (DBU).

The reaction temperatures can be varied within a substantial range. In general, the process is carried out between approximately 70 and approximately 200° C., preferably between 100 and 180° C.

The reaction can be carried out under atmospheric pressure, but also under increased pressure. In general, the reaction is carried out under pressures of between approximately 1 bar and approximately 100 bar, preferably between 1 and 10 bar.

When carrying out the process according to the invention in accordance with method B, 1 to 50 moles, preferably 1 to 30 moles, of the compound (V) are employed per mole of the compound (VI).

To prepare the esters according to the invention, the carboxylic acid on which they are based is preferably reacted in excess alcohol in the presence of strong acids such as sulphuric acid, anhydrous hydrogen chloride, methanesulphonic acid, p-toluenesulphonic acid or acid ion exchangers, at temperatures of approximately 20° to 200° C., preferably approximately 60° to 120° C. The reaction water which is formed can also be removed by azeotropic distillation with chloroform, tetrachloromethane, benzene or toluene.

Esters can also be successfully prepared by heating the acid on which they are based together with dimethylformamide dialkyl acetal in a solvent such as dimethylformamide.

The (5-methyl-2-oxo-1,3-dioxol-4-yl-methyl)esters used as prodrugs are obtained by reacting an alkali metal salt of the carboxylic acid on which they are based with 4-bromomethyl- or 4-chloromethyl-5-methyl-1,3-dioxol-2-one in a solvent such as dimethylformamide, dimethylacetamide, N-methylpyrrolidone, dimethyl sulphoxide or tetramethylurea, at temperatures of from approximately 0 to 100° C., preferably 0° to 50° C.

The acid addition salts of the compounds according to the invention are prepared in a customary manner, for example by dissolving the betain in excess aqueous acid and precipitating the salt with an organic solvent which is miscible with water such as methanol, ethanol, acetone or acetonitrile. It is also possible to heat equivalent amounts of betain and acid in water or in an alcohol such as glycol monomethyl ether and subsequently to evaporate to dryness or to filter off the precipitated salt with suction. Salts which can be used in pharmaceutics are understood as being, for example, the salts of hydrochloric acid, sulphuric acid, acetic acid, glycolic acid, lactic acid, succinic acid, citric acid, tartaric acid, methanesulphonic acid, 4-toluenesulphonic acid, galacturonic acid, gluconic acid, embonic acid, glutamic acid or aspartic acid.

For example, the alkali metal salts or alkaline earth metal salts of the carboxylic acids according to the invention are obtained by dissolving the betain in alkali metal hydroxide solution or alkaline earth metal hydroxide solution, employed in deficiency, followed by filtration of undissolved betain and evaporation of the filtrate to dryness. Salts which are suitable in pharmaceutics are sodium salts, potassium salts or calcium salts. The corresponding silver salts are obtained by reacting an alkali metal salt or alkaline earth metal salt with a suitable silver salt such as silver nitrate.

In addition to the active compounds mentioned in the examples the compounds listed by way of example in Table 1 can also be prepared. The compounds according to the invention can exist as mixtures of diastereomers as well as diastereomerically pure or enantiomerically pure compounds.

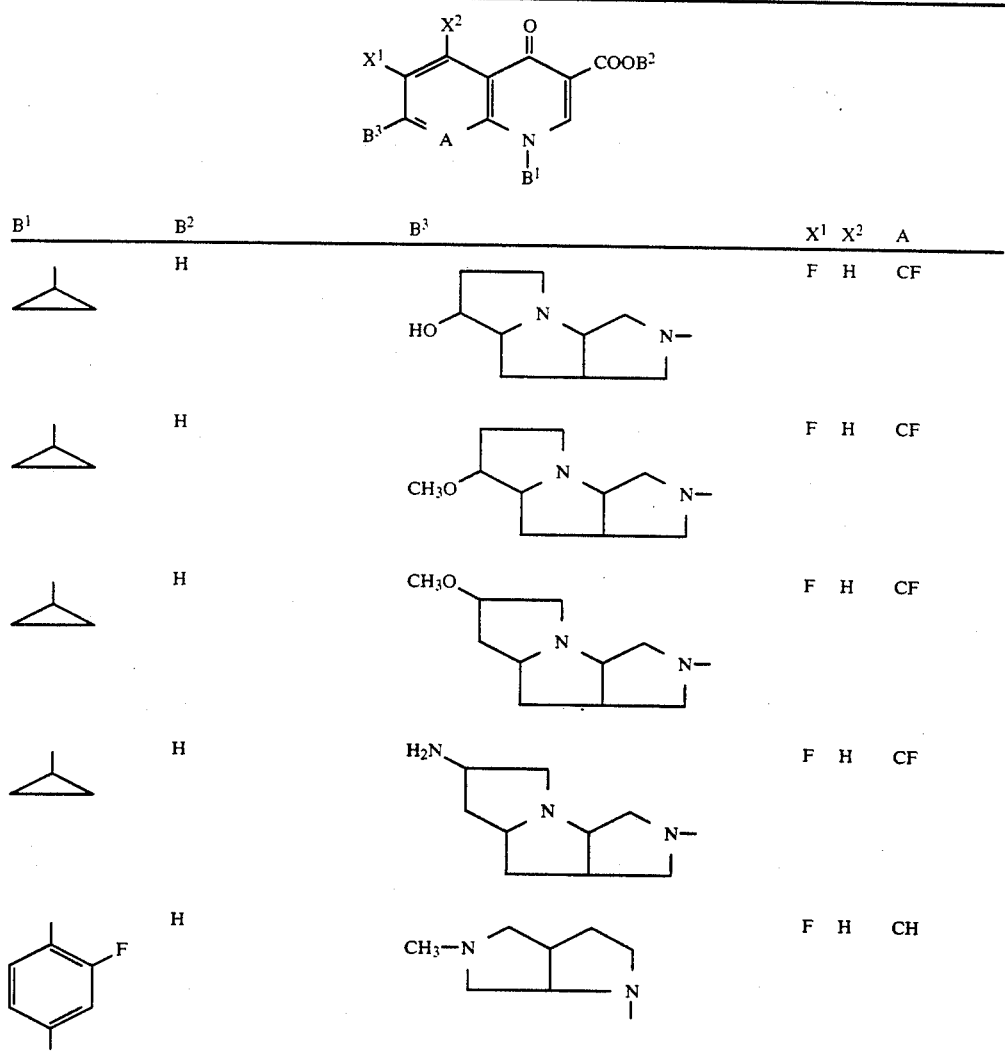

-continued

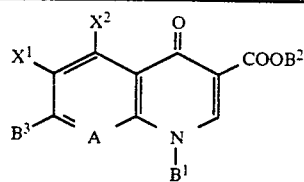

| B¹ | B² | B³ | X¹ | X² | A |
|---|---|---|---|---|---|
| 2,4-difluorophenyl | H | CH₃-N, N- (bicyclic pyrrolidine) | F | H | N |
| cyclopropyl | -CH₂-C(CH₃)=... (acetyl boronate) | CH₃-N, N- (bicyclic pyrrolidine) | F | H | CF |
| cyclopropyl | H | CH₃-N, N- (bicyclic pyrrolidine) | F | NH₂ | CF |
| cyclopropyl | H | CH₃-N, N- (bicyclic pyrrolidine) | F | CH₃ | CF |
| cyclopropyl | H | CH₃-N, N- (bicyclic pyrrolidine) | F | H | C—OCH₃ |
| cyclopropyl | H | CH₃-N, N- (pyrrolidine with OH) | F | H | CF |
| cyclopropyl | H | CH₃-N, N- (pyrrolidine with OCH₃) | F | H | CF |
| cyclopropyl | H | CH₃-N, N- (pyrrolidine with NH₂) | F | H | CF |
| cyclopropyl | H | CH₃-N, N- (pyrrolidine with CH₂F) | F | H | CF |

-continued
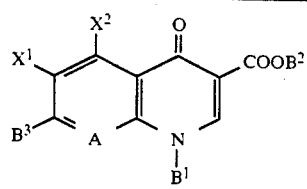
| B¹ | B² | B³ | X¹ | X² | A |
|---|---|---|---|---|---|
| △ | H | N(CH₃)-pyrrolizidine-CH₂OH | F | H | CF |
| △ | H | N(CH₃)-pyrrolizidine-CH₂OCH₃ | F | H | CF |
| △ | H | N(CH₃)-pyrrolizidine-CH₂NH₂ | F | H | CF |
| △ | H | N(CH₃)-pyrrolizidine-OH | Cl | H | CF |
| △ | H | N(CH₃)-pyrrolizidine-OCH₃ | F | NH₂ | CF |
| △ | H | N(CH₃)-pyrrolizidine-NH₂ | F | H | CH |
| △ | H | N(CH₃)-pyrrolizidine-CH₂F | F | H | N |
| △ | H | N(CH₃)-pyrrolizidine-CH₂OH | F | NH₂ | CF |

-continued

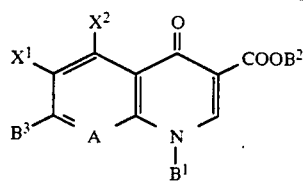

| B¹ | B² | B³ | X¹ | X² | A |
|---|---|---|---|---|---|
| cyclopropyl | C₂H₅ | N-methyl pyrrolizidine with CH₂OCH₃ | F | H | CF |
| cyclopropyl | H | N-methyl pyrrolizidine with CH₂NH₂ | F | H | CCl |
| -C₂H₅ | H | N-methyl pyrrolizidine with OH | F | H | CF |
| 2,4-difluorophenyl | H | N-methyl pyrrolizidine with OCH₃ | F | H | CF |
| cyclopropyl | H | N-methyl pyrrolizidine with NH₂ | F | H | CCl |
| cyclopropyl | -CH₂-C(CH₃)=C(O)-O-C(=O)-O- | N-methyl pyrrolizidine with CH₂F | F | H | CF |
| 2,4-difluorophenyl | H | N-methyl pyrrolizidine with CH₂OH | F | H | CF |
| 2,4-difluorophenyl | H | N-methyl pyrrolizidine with CH₂OCH₃ | F | NH₂ | CF |

-continued

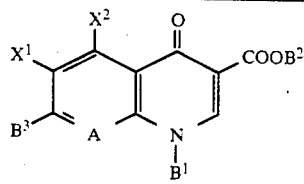

| B¹ | B² | B³ | X¹ | X² | A |
|---|---|---|---|---|---|
| 2,4-difluorophenyl | H | N-methyl-pyrrolidinyl with CH₂NH₂ | F | H | N |
| cyclopropyl | H | pyrrolidine with N-CO₂C₂H₅, N-CO₂CH₂ | F | H | CF |
| cyclopropyl | H | pyrrolidine with NH, CO₂H | F | H | CF |
| cyclopropyl | H | N-CH₃ pyrrolidine with CH₂OH | F | H | CF |
| cyclopropyl | H | pyrrolidine with N-CO₂C₂H₅, CO₂C₂H₅ | F | F | CF |
| cyclopropyl | H | N-CH₃ pyrrolidine with CH₂OH | F | F | CF |
| cyclopropyl | H | N-CH₃ pyrrolidine with CH₂OH | F | NH₂ | CF |

The compounds according to the invention have a powerful antibiotic action and, while having a low toxicity, show a broad antibacterial spectrum against gram-positive and gram-negative microorganisms, in particular against Enterobacteriaceae; mainly also against those which are resistant to various antibiotics such as, for example, penicillins, cephalosporins, aminoglycosides, sulphonamides or tetracyclins.

These valuable properties make possible their use as chemotherapeutical active compounds in medicine as well as preservatives of inorganic and organic materials, in particular of a wide range of organic materials, for example polymers, lubricants, paints, fibres, leather, paper and wood, of foodstuffs and of water.

The compounds according to the invention are active against a very broad spectrum of microorganisms. It is possible, with their aid, to control gram-negative and gram-positive bacteria and bacteria-like microorganisms and to prevent, alleviate and/or cure the diseases caused by these pathogens.

The compounds according to the invention are particularly effective against bacteria and bacteria-like microorganisms. They are therefore particularly suitable in human and veterinary medicine for the prophylaxis and chemotherapy of local and systemic infections which are caused by these pathogens.

The compounds according to the invention can be administered in a range of pharmaceutical preparations. Preferred pharmaceutical preparations which may be mentioned are tablets, coated tablets, capsules, pills, granules, suppositories, solutions, suspensions, emulsions, pastes, ointments, gels, creams, lotions, powders and sprays.

The minimum inhibitory concentrations (MIC) were determined by means of serial dilution tests on Iso-Sensitest agar (Oxoid). For each test substance, a two-fold dilution series of agar plates was prepared, with decreasing concentrations of the active compound in each case. The agar plates were inoculated with a multipoint inoculator (Denley). For inoculation, overnight cultures of the pathogens were used which had been previously been diluted in such a way that each point of inoculation contained approximately 10 colony-forming particles. The inoculated agar plates were incubated at 37° C., and the growth of microorganisms was read off after approximately 20 hours. The MIC value (μg/ml) indicates the lowest concentration of active compound at which no growth could be observed with the naked eye.

The table which follows lists the MIC values of some of the compounds according to the invention in comparison with 1-cyclopropyl-7-(2,3-dimethyl-2,7-diazabicyclo[3.3.0]oct-7-yl-6,8-difluoro-1,4-dihydro-4-oxo-3-quinolinecarboxylic acid hydrochloride (Example 37 b in EP-A-0,350,733):

MIC values (mg/1) determined by agar dilution test (Denley multipoint inoculator; Iso-Sensitest agar)

| Test strain | Example | | | |
|---|---|---|---|---|
| | 16 | 27 | 14 | Comparison* |
| E.coli Neumann | 0.06 | 0.03 | 0.06 | 0.125 |
| Proteus mirabils 8175 | 0.5 | 0.5 | 0.5 | 1 |
| Providencia sp. 12012 | 0.25 | 0.25 | 0.25 | 0.5 |
| Staphylococcus aureus ICB 25 701 | 2 | 4 | 8 | 16 |

*Example 37b of EP-A-0.350.733

PREPARATION OF THE INTERMEDIATES

Example A

2-Benzyl-2,7-diazabicyclo[3.3.0]octane

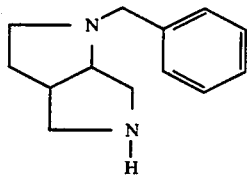

a) Ethyl N-(2,2-dimethoxyethyl)-carbamidate 214 g (2 mol) of ethyl chloroformate are added dropwise at 10° C. to 214 g (2 mol) of aminoacetaldehyde dimethyl acetal in 1 l of toluene and 90 g of NaOH in 500 ml of water. Stirring of the mixture is continued for 2 hours at room temperature, and the aqueous phase is separated off, saturated with sodium chloride and extracted with toluene. The toluene solutions are dried over magnesium sulphate, concentrated and distilled.

Yield: 338 g (95.4% of theory)
Boiling point: 60° C./0.03 mbar b) Ethyl N-allyl-N-(2,2-dimethoxyethyl)-carbamidate 500 g (2.82 mol) of ethyl N-(2,2-dimethoxyethyl)-carbamidate, 625 g of pulverulent potassium hydroxide and 10 g of triethylbenzylammonium chloride are initially introduced into 2.7 l of toluene, and 345 g (2.85 mol) of allyl bromide are added dropwise at room temperature. The mixture is stirred overnight at room temperature, the salts are filtered off with suction, and the filtrate is washed once using saturated sodium chloride solution, dried over potassium carbonate, concentrated and distilled.

Yield: 582 g (95% of theory)
Boiling point: 64° C./0.1 mbar c) Ethyl N-allyl-N-(2-oxoethyl)-carbamidate 68 g (0.313 mol) of ethyl N-allyl-N-(2,2-dimethoxyethyl)-carbamidate together with 150 ml of formic acid are heated for one hour at 100° C. The mixture is poured onto ice and extracted several times using methylene chloride, and the organic phases are washed using sodium hydrogen carbonate solution, dried over magnesium sulphate, concentrated and distilled.

Yield: 46.7 g (87.2% of theory)
Boiling point: 58° C./0.09 mbar d) N-benzylglycine 225.8 g (1.17 mol) of ethyl N-benzylglycinate (J. Am. Chem. Soc. 72, 1238 (1950)) are refluxed overnight in 600 ml of water. The product which has crystallised out is filtered off with suction and the filtrate is extracted once using tert.-butyl methyl ether. The aqueous phase is concentrated and the crystals obtained together with the product which has been filtered off are dried in a desiccator over phosphorus pentoxide.

Yield: 184 g (95% of theory)
Melting point: 199° C.

e) Ethyl 2-benzyl-2,7-diazabicyclo[3.3.0]octane-7-carboxylate 42.8 g (0.25 mol) of ethyl N-allyl-N-(2-oxoethyl)carbamidate together with 41.3 g (0.25 mol) of N-benzylglycine are refluxed overnight in 750 ml of toluene. The mixture is concentrated, and the residue is distilled.

Yield: 59.6 g (87% of theory)
Boiling point: 140° C./0.09 mbar f) 2-Benzyl-2,7-diazabicyclo[3.3.3]octane 55.6 g (0.2 mol) of ethyl 2-benzyl-2,7-diazabicyclo[3.3.0]octane-7-carboxylate together with 300 ml of concentrated hydrochloric acid are refluxed overnight. The batch is then rendered alkaline using potassium carbonate and extracted five times using 100 ml portions of chloroform, and the extracts are dried over potassium carbonate, concentrated and distilled.

Yield: 31 g (76.6% of theory)
Boiling point: 105° C./0.45 mbar

Example B

Ethyl 2,7-diazabicyclo[3.3.0]octane-2-carboxylate

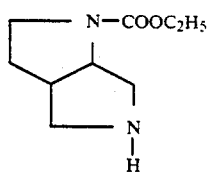

a) Tert.-butyl 2-benzyldiazabicyclo[3.3.0]octane-7-carboxylate 20.2 g (0.1 mol) of 2-benzyl-2,7-diazabicyclo[3.3.0]octane are dissolved in 125 ml of tert.-butanol, a solution of 4.2 g of sodium hydroxide in 100 ml of water is added, and 23 g (0.105 mol) of di-tert.-butyl pyrocarbonate are added dropwise at room temperature. The mixture is stirred overnight at room temperature, extracted five times using 100 ml portions of chloroform, and the extracts are dried over potassium carbonate, concentrated and distilled.

Yield: 24.8 g (82% of theory)
Boiling point: 145°-149° C/0.8 mbar b) Tert.-butyl 2,7-diazabicyclo[3.3.0]octane-7-carboxylate 24 g (79.4 mmol) of tert.-butyl 2-benzyldiazabicyclo[3.3.0]octane-7-carboxylate in 400 ml of ethanol are hydrogenated on 3 g of palladium/active carbon (10% Pd) at 100° C. and 100 bar. The catalyst is filtered off, the filtrate is concentrated, and the residue is distilled.

Yield: 13.1 g (77.7% of theory)
Boiling point: 87° C./0.1 mbar c) 2-Ethyl7-tert.-butyl2,7-diazabicyclo[3.3.0]octane-2,7-dicarboxylate 13 g (61.2 mmol) of tert.-butyl 2,7-diazabicyclo[3.3.0]octane-7-carboxylate are dissolved in 100 ml of toluene, a solution of 3 g of sodium hydroxide in 20 ml of water is added, and 7 g (64.5 mmol) of ethyl chloroformate are added dropwise at room temperature. The mixture is stirred for 3 hours at room temperature, and the aqueous phase is separated off and extracted twice using 100 ml portions of methylene chloride. The organic solutions are dried over magnesium sulphate, concentrated and distilled.

Yield: 16 g (91.9% of theory)
Boiling point: 125° C./0.13 mbar d) Ethyl 2,7-diazabicyclo[3.3.0]octane-2-carboxylate 15.2 g (53.5 mmol) of 2-ethyl 7-tert.-butyl 2,7-diazabicyclo[3.3.0]octane-2,7-dicarboxylate in 100 ml of chloroform are refluxed for 5 hours together with 10.5 g (55.3 mol) of para-toluenesulphonic acid. The mixture is washed with 50 ml of 10% strength sodium hydroxide solution, and the organic phase is dried over potassium carbonate, concentrated and distilled.

Yield: 9.5 g (96.4% of theory)
Boiling point: 80°-90° C./0.1 mbar

Example C

2-Methyl-2,7-diazabicyclo[3.3.0]octane

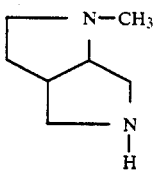

a) Methyl 2-methyl-2,7-diazabicyclo[3.3.0]octane-7-carboxylate 8.6 g (50 mmol) of ethyl N-allyl-N-(2-oxoethyl)-carbamidate together with 4.5 g (50 mmol) of sarcosine in 200 ml of toluene are refluxed overnight. The mixture is concentrated and the residue is distilled.

Yield: 7.5 g (75.7% of theory)
Boiling point: 80°-82° C./0.1 mbar b) 2-Methyl-2,7-diazabicyclo[3.3.0]octane 9 g (45.4 mmol) of ethyl 2-methyl-2,7-diazabicyclo[3.3.0]octane-7-carboxylate together with 50 ml of concentrated hydrochloric acid are refluxed overnight. The batch is rendered alkaline using potassium carbonate and extracted ten times using 50 ml portions of chloroform, and the extracts are dried over potassium carbonate, concentrated and distilled.

Yield: 4.5 g (78% of theory)
Boiling point: 72° C./25 mbar

Example D

2-Phenyl-2,7-diazabicyclo[3.3.0]octane

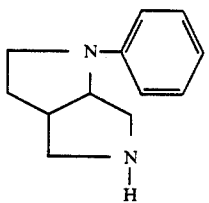

a) Ethyl 2-phenyl-2,7-diazabicyclo[3.3.0]octane-7-carboxylate 8.6 g (50 mmol) of ethyl N-allyl-N-(2-oxoethyl)carbamidate and 7.6 g (50 mmol) of phenylglycine are refluxed overnight in 200 ml of toluene. The liquid phase is decanted off the resinous material and concentrated, and the residue is distilled.

Yield: 8.1 g (62.2% of theory)
Boiling point: 151° C./0.12 mbar b) 2-Phenyl-2,7-diazabicyclo[3.3.0]octane 7.6 g (31.6 mmol) of ethyl 2-phenyl-2,7-diazabicyclo[3.3.0]octane-7-carboxylate together with 50 ml of concentrated hydrochloric acid are refluxed overnight. The mixture is concentrated, the residue is taken up in 50 ml of 10% strength sodium hydroxide solution, and this mixture is extracted five times using 50 ml portions of chloroform. The extracts are dried over potassium carbonate and concentrated, and the residue is distilled.

Yield: 3.7 g (62% of theory)
Boiling point: 103° C./0.08 mbar

Example E

3-Methyl-2,7-diazabicyclo[3.3.0]octane

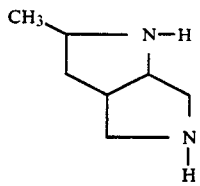

a) N-benzylalanine 333 g (1.72 mol) of methyl N-benzylalaninate (J. Chem. Soc. 4374 (1952)) are refluxed overnight together with 860 ml of water. Precipitated product is filtered off with suction, and the filtrate is extracted once using tert.-butyl methyl ether. The aqueous solution is concentrated, and the crystals obtained and the first crystal fraction are dried in a desiccator over phosphorus pentoxide.

Yield: 280 g (91% of theory)
Melting point: 270°–276° C. (decomposition)

b) Ethyl 2-benzyl-3-methyl-2,7-diazabicyclo[3.3.0]octane-7-carboxylate 42.8 g (0.25 mol) of ethyl N-allyl-N-(2-oxoethyl)carbamidate together with 44.8 g (0.25 mol) of N-benzylalanine are refluxed overnight in 750 ml of toluene. The mixture is concentrated, and the residue is distilled twice.

Yield: 32 g (44.4% of theory)
Boiling point: 128°–133° C./0.06 mbar
96% of the product comprises a stereoisomer.

c) Ethyl 3-methyl-2,7-diazabicyclo[3.3.0]octane-7-carboxylate 32 g (0.11 mol) of ethyl 2-benzyl-3-methyl-2,7-diazabicyclo[3.3.0]octane-7-carboxylate in 560 ml of ethanol are hydrogenated on 4.5 g of palladium/active carbon at 100° C. and 100 bar. The catalyst is filtered off with suction, the filtrate is concentrated, and the residue is distilled.

Yield: 17.1 g (77.7% of theory)
Boiling point: 140°–145° C./8 mbar d) 3-Methyl-2,7-diazabicyclo[3.3.0]octane 17 g (85.7 mmol) of ethyl 3-methyl-2,7-diazabicyclo[3.3.0]octane-7-carboxylate together with 100 ml of concentrated hydrochloric acid are refluxed overnight. The mixture is concentrated, the concentrate is taken up in 50 ml of water, and the mixture is rendered alkaline using potassium carbonate and extracted ten times using 50 ml portions of chloroform. The extracts are dried over potassium carbonate and concentrated, and the residue is distilled.

Yield: 6 g (55% of theory)
Boiling point: 68°–70° C./6 mbar

Example F 2,3-Dimethyl-2,7-diazabicyclo[3.3.0]octane

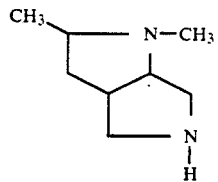

a) Ethyl 2,3-dimethyl-2,7-diazabicyclo[3.3.0]octane-7-carboxylate 17.2 g (0.1 mol) of ethyl N-allyl-N-(2-oxoethyl)carbamidate together with 10.5 g (0.1 mol) of N-methylalanine in 300 ml of toluene are refluxed overnight. The mixture is concentrated, and the residue is distilled.

Yield: 11.3 g (53.2% of theory)
Boiling point: 81° C./0.25 mbar b) 2,3-Dimethyl-2,7-diazabicyclo[3.3.0]octane 7.25 g (34.2 mmol) of ethyl 2,3-dimethyl-2,7-diazabicyclo[3.3.0]octane-7-carboxylate together with 50 ml of concentrated hydrochloric acid are refluxed overnight. The mixture is rendered alkaline using potassium carbonate and extracted ten times using 50 ml portions of chloroform, the extracts are dried over potassium carbonate and concentrated, and the residue is distilled.

Yield: 3 g (62.5% of theory)
Boiling point: 72°–74° C./10 mbar

Example G 2,8-Dimethyl-2,7-diazabicyclo[3.3.0]octane

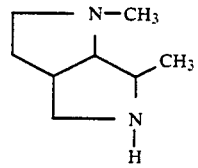

a) Ethyl N-(1,1-dimethoxyprop-2-yl)-carbamidate 80 g (0.73 mol) of ethyl chloroformate are added dropwise with ice-cooling to 86.2 g (0.72 mol) of 2-aminopropionaldehyde dimethyl acetal in 350 ml of toluene and 32 g (0.8 mol) of NaOH in 300 ml of water. Stirring is continued for 2 hours at room temperature, the organic phase is separated off, the aqueous phase is extracted using toluene, and the toluene solutions are dried over $K_2CO_3$. The solution is concentrated and distilled.

Yield: 132 g (95% of theory)
Boiling point: 55° C./0.06 mbar b) Ethyl N-allyl-N-(1,1-dimethoxyprop-2-yl)-carbamidate 151 g (0.79 mol) of ethyl N-(1,1-dimethoxyprop-2-yl)-carbamidate, 175 g of pulverulent potassium hydroxide and 2.8 g of triethylbenzylammonium chloride are initially introduced into 750 ml of toluene, and 94 g (0.777 mol) of allyl bromide are added dropwise at room temperature. The mixture is stirred overnight at room temperature, and a further 10 g (82.6 mmol) of allyl bromide are then added dropwise, and the mixture is stirred for one day at room temperature. Water is added until all salts have dissolved, and the aqueous phase is separated off and extracted twice using 150 ml portions of toluene. The extracts are dried over $K_2CO_3$, and concentrated, and the residue is distilled.

Yield: 173 g (94.7% of theory)
Boiling point: 68° C./0.1 mbar c) Allyl-(1,1-dimethoxyprop-2-yl)-amine 20 g of molecular sieve are added to 12 g (0.1 mol) of 1,1-dimethoxyacetone in 100 ml of ethanol, and 7 g (0.12 mol) of allylamine are then added dropwise. The mixture is allowed to stand overnight at room temperature, the liquid phase is decanted off from the molecular sieve and cooled to 0° C. in an ice-bath, and 4 g (0.1 mol) of sodium borohydride are added in small portions. The mixture is stirred overnight at room temperature, concentrated and taken up in 100 ml of water, and this mixture is saturated with potassium carbonate and extracted five times using 100 ml portions of chloroform. The extracts are dried over potassium carbonate, concentrated and distilled.

Yield: 10.3 g (64.7% of theory)
Boiling point: 75° C./25 mbar d) Ethyl N-allyl-N-(1,1-dimethoxyprop-2-yl)-carbamidate 125 g (0.785 mol) of allyl-(1,1-dimethoxyprop-2-yl)amine are initially introduced into 400 ml of toluene, a solution of 40 g of sodium hydroxide in 200 ml of water is added, the mixture is cooled to 0° C. in an ice-bath, and 95 g (0.876 mol) of ethyl chloroformate are added dropwise. The mixture is subsequently stirred for 3 hours at room temperature, the aqueous phase is separated off and extracted twice using 100 ml portions of toluene. The extracts are dried over potassium carbonate, concentrated, and distilled.

Yield: 170.8 g (94% of theory)
Boiling point: 55° C./0.05 mbar e) Ethyl N-allyl-N-(1-oxoprop-2-yl)-carbamidate 182 g (0.787 mol) of ethyl N-allyl-N-(1,1-dimethoxyprop-2-yl)-carbamidate together with 80 ml of formic acid are refluxed for 3 hours in 1.5 l of water. The batch is saturated with sodium chloride, the organic phase is separated off, and the aqueous phase is extracted twice using 500 ml portions of methylene chloride. The organic solutions are washed to neutrality using saturated sodium hydrogen carbonate solution, dried over magnesium sulphate, concentrated and distilled.

Yield: 134 g (91.9% of theory)
Boiling point: 65° C./0.23 mbar f) Ethyl 2,8-dimethyl-2,7-diazabicyclo[3.3.0]octane-7-carboxylate

On a water separator, 18.5 g (0.1 mol) of ethyl N-allyl-N-(1-oxoprop-2-yl)-carbamidate together with 9 g (0.1 mol) of sarcosine are refluxed overnight in 300 ml of toluene. The mixture is concentrated, and the residue is distilled.

Yield: 17 g (80% of theory)
Boiling point: 140°-150° C./8 mbar g) 2,8-Dimethyl-2,7-diazabicyclo[3.3.0]octane 16.9 g (79.6 mol) of ethyl 2,8-dimethyl-2,7-diazabicyclo[3.3.0]octane-7-carboxylate together with 130 ml of concentrated hydrochloric acid are refluxed overnight. The mixture is concentrated, the concentrate is taken up in 50 ml of water, and this mixture is rendered alkaline using potassium carbonate and extracted five times using 50 ml portions of chloroform. The extracts are dried over potassium carbonate and concentrated, and the residue is distilled.

Yield: 6.6 g (58.5% of theory)
Boiling point: 60°-62° C./6 mbar

Example H

5-Chloro-2-methyl-2,7-diazabicyclo[3.3.0]octane

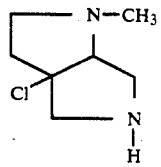

a) Ethyl N-(2-chloroallyl)-N-(2,2-dimethoxyethyl)carbamidate 115 g (0.65 mol) of ethyl N-(2,2-dimethoxyethyl)carbamidate 130 g of pulverulent potassium hydroxide and 2 g of triethylbenzylammonium chloride are initially introduced into 650 ml of toluene, and 142 g (0.7 mol) of 2-chloroallyl iodide are added dropwise at room temperature. After the mixture has been stirred overnight, a gas chromatogram showed that the reaction was incomplete, and therefore another 65 g of pulverulent potassium hydroxide and 1 g of triethylbenzylammonium chloride were added and a further 71 g (0.35 mol) of 2-chloroallyl iodide were added dropwise. After the mixture had been stirred overnight at room temperature, the salts were filtered off with suction, the filtrate was washed with saturated sodium chloride solution, dried over magnesium sulphate and concentrated, and the residue was distilled.

Yield: 140.9 g (86% of theory)
Boiling point: 92°-97° C./0.8 mbar b) Ethyl N-(2-chloroallyl)-N-(2-oxoethyl)-carbamidate 151 g (0.6 mol) of ethyl N-(2-chloroallyl)-N-(2,2-dimethoxyethyl)-carbamidate together with 60 ml of formic acid are refluxed for three hours in 1.2 l of water. The mixture is saturated with sodium chloride, and the aqueous phase is separated off and extracted twice using 300 ml portions of methylene chloride. The organic phases are washed to neutrality using saturated sodium hydrogen carbonate solution, dried over magnesium sulphate, concentrated and distilled.

Yield: 97.1 g (78% of theory)
Boiling point: 88°-91° C./0.06 mbar c) Ethyl 5-chloro-2-methyl-2.7-diazabicyclo[3.3.0]octane-7-carboxylate 10.3 g (50 mmol) of ethyl N-(2-chloroallyl)- N-(2-oxoethyl)-carbamidate together with 4.5 g (50 mmol) of sarcosine are refluxed overnight in 200 ml of toluene. The mixture is concentrated, and the residue is distilled.

Yield: 10.6 g (91% of theory)

Boiling point: 80° C./0 1 mbar d) 5-Chloro-2-methyl-2,7-diazabicyclo[3.3.0]octane 9.3 g (40 mmol) of ethyl 5-chloro-2-methyl-2,7-diazabicyclo[3.3.0]octane-7-carboxylate are refluxed overnight together with 50 ml of concentrated hydrochloric acid. The mixture is concentrated, the concentrate is taken up in 30 ml of water, and this mixture is rendered alkaline using potassium carbonate and extracted five times using 50 ml portions of chloroform. The extracts are dried over potassium carbonate, concentrated and distilled.

Yield: 4.7 g (72% of theory)
Boiling point: 73° C./4 mbar

Example I

5-Chloro-2,3-dimethyl-2,7-diazabicyclo[3.3.0]octane

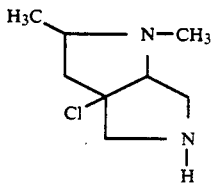

a) Ethyl 5-chloro-2,3-dimethyl-2,7-diazabicyclo[3.3.0]octane-7-carboxylate 10.3 g (50 mmol) of ethyl N-(2-chloroallyl)-N-(2-oxoethyl)-carbamidate together with 5.2 g (50.5 mmol) of N-methylalanine are refluxed overnight in 200 ml of toluene. The mixture is concentrated, and the residue is distilled.

Yield: 8.1 g (65.7% of theory)
Boiling point: 87° C./0.08 mbar b) 5-Chloro-2,3-dimethyl-2,7-diazabicyclo[3.3.0]octane 7.6 g (30.8 mmol) of ethyl 5-chloro-2,3-dimethyl-2,7-diazabicyclo[3.3.0]octane-7-carboxylate together with 30 ml of concentrated hydrochloric acid are refluxed overnight. The mixture is concentrated, the concentrate is taken up in 30 ml of water, this mixture is rendered alkaline using potassium carbonate and extracted five times using 50 ml portions of chloroform, and the extracts are dried over potassium carbonate, concentrated and distilled.

Yield: 3.7 g (68.4% of theory)
Boiling point: 95°-97° C./6 mbar

Example J 1,4-Diazatricyclo6.2.0.0$^{2,6}$]decane

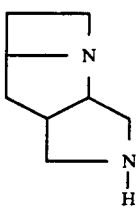

a) Ethyl 1,4-diazatricyclo6.2.0.0$^{2,6}$]decane-4-carboxylate

On a water separator, 17.1 g (0.1 mol) of ethyl N-allyl-N-(2-oxoethyl)-carbamidate together with 10 g (0.1 mol) of azetidine-2-carboxylic acid are refluxed overnight in 200 ml of toluene. Unreacted amino acid is filtered off with suction, the filtrate is concentrated, and the residue is distilled.

Yield: 13.8 g (65.6% of theory)
Boiling point: 108° C./0.35 mbar b) 1,4-diazatricyclo6.2.0.0$^{2,6}$]decane 13.7 g (65.1 mmol) of ethyl 1,4-diazatricyclo[6.2.0.0$^{2,6}$]decane-4-carboxylate together with 42 g of Ba(OH)$_2$×8H$_2$O are refluxed overnight in 150 ml of water. Potassium carbonate is added, barium carbonate is filtered off with suction, and the filtrate is extracted ten times using 100 ml portions of chloroform. The extracts are dried over potassium carbonate and concentrated, and the residue is distilled.

Yield: 5.3 g (58.9% of theory)
Boiling point: 85° C./6 mbar

Example K 1,4-diazatricyclo[6.3.0.0$^{2,6}$]undecane

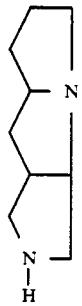

a) Ethyl 1,4-diazatricyclo6.3.0.0$^{2,6}$]undecane-4-carboxylate 8.6 g (50 mmol) of ethyl N-allyl-N-(2-oxoethyl)carbamidate together with 5.8 g (50 mmol) of proline are refluxed overnight in 200 ml of toluene. The mixture is concentrated, and the residue is distilled.

Yield: 9.6 g (86% of theory)
Boiling point: 102°-112° C./0.13-0.15 mbar b) 1,4-Diazatricyclo[6.3.0.0$^{2,6}$]undecane 9 g (40 mmol) of ethyl 1,4-diazatricyclo[6.3.0.0$^{2,6}$]undecane-4-carboxylate together with 50 ml of concentrated hydrochloric acid are refluxed overnight. The mixture is rendered alkaline using potassium carbonate and extracted ten times using 50 ml portions of chloroform, the extracts are dried over potassium carbonate and concentrated, and the residue is distilled.

Yield: 4.9 g (80.5% of theory)
Boiling point: 50° C./0.05 mbar

Example L

10-Hydroxy-1,4-diazatricyclo6.3.0.0$^{2,6}$]undecane

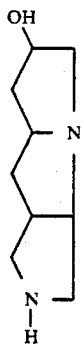

a) Ethyl 10-hydroxy-1,4-diazatricyclo[6.3.0.0$^{2,6}$]undecane-4-carboxylate 8.6 g (50 mmol) of ethyl N-allyl-N-(2-oxoethyl)carbamidate together with 6.6 g (50 mmol) of trans-4-hydroxyproline in 200 ml of dimethylformamide are heated overnight to 120° C. The mixture is concentrated, and the residue is distilled.

Yield: 9.7 g (81% of theory)
Boiling point: 170° C./0.3 mbar
The product consists mostly of two stereoisomers in the ratio 1:1.

b) 10-Hydroxy-1,4-diazatricyclo6.3.0.0$^{2,6}$]undecane 8 g (33.3 mmol) of ethyl 10-hydroxy-1,4-diazatricyclo[6.3.0.0$^{2,6}$]undecane-4-carboxylate together with 21 g of Ba(OH)$_2$×8H$_2$O are refluxed overnight in 150 ml of water. The mixture is saturated with potassium carbonate, barium carbonate is filtered off with suction, and the mixture is extracted ten times using 100 ml portions of chloroform. The extracts are dried over potassium carbonate, concentrated and distilled.

Yield: 4.6 g (82% of theory)
Boiling point: 110°-115° C./0.1 mbar

Example M 1,4-Diazatricyclo6.4.0.0$^{2,6}$]dodecane

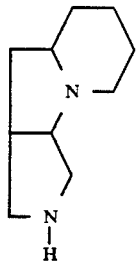

a) Ethyl 1 4-diazatricyclo6.4.0.0$^{2,6}$]dodecane-4-carboxylate 17.1 g (0.1 mol) of ethyl N-allyl-N-(2-oxoethyl)carbamidate together with 13 g (0.1 mol) of piperidine-2-carboxylic acid are refluxed overnight in 200 ml of toluene. The mixture is concentrated, and the residue is distilled.

Yield: 20.8 g (87.2% of theory)
Boiling point: 105°-112° C./0.12 mbar b) 1.4-Diazatricyclo6.4.0.0$^{2,6}$]decane 20.7 g (86.8 mmol) of ethyl 1,4-diazatricyclo[6.4.0.0$^{2,6}$]dodecane-4-carboxylate are refluxed overnight together with 250 ml of concentrated hydrochloric acid. The mixture is concentrated, the concentrate is taken up in 50 ml of water, and this mixture is rendered alkaline using potassium carbonate. The mixture is extracted ten times using 50 ml portions of chloroform, and the extracts are dried over potassium carbonate and concentrated, and the residue is distilled.

Yield: 8.5 g (58.9% of theory)
Boiling point: 108° C./8 mbar

Example N

10-Thia-1,4-diazatricyclo6.3.0.0$^{2,6}$]undecane

a) Ethyl 10-thia-1,4-diazatricyclo[6.3.0.0$^{2,6}$]undecane-4-carboxylate 17.2 g (0.1 mol) of ethyl N-allyl-N-(2-oxoethyl)carbamidate together with 13.5 g (0.1 mol) of thiazolidine-4-carboxylic acid are refluxed overnight in 300 ml of toluene. The mixture is concentrated and distilled.

Yield: 20 g (82.5% of theory)
Boiling point: 155°-156° C./0.5 mbar b) 10-Thia-1,4-diazatricyclo6.3.0.0$^{2,6}$]undecane 12.5 g (50 mmol) of ethyl 10-thia-1,4-diazatricyclo[6.3.0.0$^{2,6}$]undecane-4-carboxylate together with 32 g of Ba(OH)$_2$×8H$_2$O are refluxed overnight in 225 ml of water. Potassium carbonate is added, barium carbonate is filtered off with suction, and the filtrate is extracted ten times using 100 ml portions of chloroform. The extracts are dried over potassium carbonate, concentrated and distilled.

Yield: 6.2 g (72.8% of theory)
Boiling point: 90°-94° C./0.05 mbar

Example O 9,9-Dimethyl-10-thia-1,4-diazatricyclo6.3.0.0$^{2,6}$]undecane

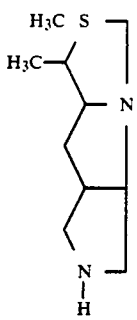

a) Ethyl 9,9-dimethyl-10-thia-1,4-diazatricyclo[6.3.0.0$^{2,6}$]undecane-4-carboxylate 8.6 g (50 mmol) of ethyl N-allyl-N-(2-oxoethyl)carbamidate together with 8.1 g (50 mmol) of 5,5-dimethyl-thiazolidine-4-carboxylic acid are refluxed overnight in 200 ml of toluene. The mixture is concentrated and the residue is distilled.

Yield: 8.4 g (62.2% of theory)
Boiling point: 141°-155° C./0.03-0.05 mbar b) 9,9-Dimethyl-10-thia-1,4-diazatricyclo6.3.0.0$^{2,6}$]undecane 6 g (22.2 mmol) of ethyl 9,9-dimethyl-10-thia-1,4-diazatricyclo[6.3.0.0$^{2,6}$]undecane-4-carboxylate together with 12 g of Ba(OH)$_2 \times$ 8H$_2$O are refluxed overnight in 100 ml of water. Potassium carbonate is added, barium carbonate is filtered off with suction, and the filtrate is extracted ten times using 100 ml portions of chloroform. The extracts are dried over potassium carbonate and concentrated, and the residue is distilled.

Yield: 2.25 g (51% of theory)
Boiling point: 83° C./0.02 mbar

Example P

7-Methyl-2,7-diazabicyclo[3.3.0]octane

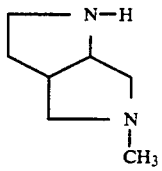

a) 2-Benzyl-7-methyl-2,7-diazabicyclo[3.3.0]octane 13.7 g (50 mmol) of ethyl 2-benzyldiazabicyclo[3.3.0]octane-7-carboxylate in 20 ml of absolute tetrahydrofuran are added dropwise to 3.8 g (0.1 mol) of lithium aluminum hydride in 100 ml of absolute tetrahydrofuran. The mixture is refluxed overnight and decomposed in succession with in each case 4 ml of water, 15% strength potassium hydroxide solution and water. The inorganic salts are filtered off with suction and extracted three times by boiling with 50 ml portions of tetrahydrofuran. The organic solutions are concentrated and the residue is distilled.

Yield: 10.4 g (96% of theory)
Boiling point: 90°-100° C./0.1 mbar b) 7-Methyl-2,7-diazabicyclo[3.3.0]octane 10.3 g (47.6 mmol) of 2-benzyl-7-methyl-2,7-diazabicyclo[3.3.0]octane in 200 ml of ethanol are hydrogenated on 2.5 g of palladium/active carbon (10% Pd) at 100° C. and 100 bar. The catalyst is filtered off with suction, the filtrate is concentrated, and the residue is distilled.

Yield: 4.2 g (69.9% of theory)
Boiling point: 50°-53° C./6 mbar

Example Q

2-Benzyl-8-methyl-2,7-diazabicyclo[3.3.0]octane

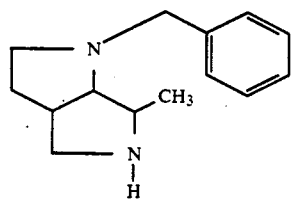

a) Ethyl 2-benzyl-8-methyl-2,7-diazabicyclo[3.3.0]octane-7-carboxylate 37 g (0.2 mol) of ethyl N-allyl-N-(1-oxo-2-propyl)carbamidate together with 33 g (0.2 mol) of N-benzylglycine are refluxed overnight in 500 ml of toluene on a water separator. The batch is concentrated and the residue is distilled.

Yield: 48.5 g (84% of theory)
Boiling point: 140°-145° C./0.2 mbar

Gas chromatography reveals that the product is a uniform stereoisomer.

b) 2-Benzyl-8-methyl-2,7-diazabicyclo[3.3.0]octane 16 g (55 mmol) of ethyl 2-benzyl-8-methyl-2,7-diazabicyclo[3.3.0]octane-7-carboxylate are refluxed overnight with 50 ml of concentrated hydrochloric acid. The batch is concentrated and dissolved in 50 ml of water, and the mixture is rendered alkaline using potassium carbonate. The mixture is extracted five times using 50 ml portions of chloroform, the extracts are dried over K$_2$CO$_3$ and concentrated, and the residue is distilled.

Yield: 7.9 g (66.4% of theory)
Boiling point: 108°-113° C./0.17 mbar

Example R

8-Methyl-2,7-diazabicyclo[3.3.0]octane

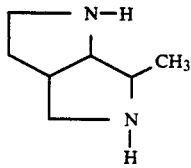

7.8 g (36 mmol) of 2-benzyl-8-methyl-2,7-diazabicyclo[3.3.0]octane in 200 ml of ethanol are hydrogenated on 2 g of palladium/active carbon (10% Pd) at 100° C. and 100 bar. The catalyst is filtered off with suction, the filtrate is concentrated, and the residue is distilled. The distillate crystallises.

Yield: 3.3 g (72.7% of theory)
Boiling point: 110° C./30 mbar
Melting point: 72°–75° C.

Example S

Ethyl 8-methyl-2,7-diazabicyclo[3.3.0]octane-7-carboxylate

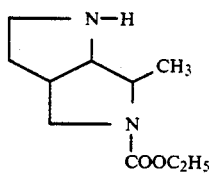

16 g (55 mmol) of ethyl 2-benzyl-8-methyl-2,7-diazabicyclo[3.3.0]octane-7-carboxylate in 300 ml of ethanol are hydrogenated on 3 g of palladium/active carbon (10% Pd) at 100° C. and 100 bar. The catalyst is filtered off with suction, the filtrate is concentrated, and the residue is distilled.

Yield: 9.7 g (89% of theory)
Boiling point: 100° C./0.1 mbar

Example T 7.8-Dimethyl-2,7-diazabicyclo[3.3.0]octane

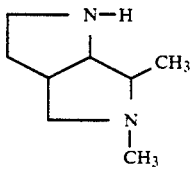

a) 2-Benzyl-7,8-dimethyl-2,7-diazabicyclo[3.3.0]octane 14.4 g (50 mmol) of ethyl 2-benzyl-8-methyl-2,7-diazabicyclo[3.3.0]octane-7-carboxylate in 20 ml of absolute tetrahydrofuran are added dropwise to 3.8 g (0.1 mol) of lithium aluminum hydride in 100 ml of absolute tetrahydrofuran, and the mixture is subsequently refluxed overnight. The mixture is decomposed in succession with in each case 4 ml of water, 15% strength potassium hydroxide solution and water, and the inorganic salts are filtered off with suction and extracted three times by boiling with 50 ml portions of tetrahydrofuran. The organic solutions are concentrated, and the residue is distilled.

Yield: 10.9 g (94.6% of theory)
Boiling point: 105° C./0.08 mbar b) 7,8-Dimethyl-2,7-diazabicyclo[3.3.0]octane 10.8 g (46.9 mmol) of 2-benzyl-7,8-dimethyl-2,7-diazabicyclo[3.3.0]octane in 200 ml of ethanol are hydrogenated on 2.5 g of palladium/active carbon at 100° C. and 100 bar. The catalyst is filtered off with suction, the filtrate is concentrated, and the residue is distilled.

Yield: 4.3 g (65.4% of theory)
Boiling point: 60°–62° C./6 mbar

Example U

4-Methyl-2,7-diazabicyclo[3.3.0]octane

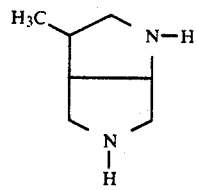

a) N-(2-butene-1-yl)-N-(2,2-dimethoxyethyl)-amine 200 g of molecular sieve are initially introduced into 1000 ml of ethanol, and 105 g (1 mol) of aminoacetaldehyde dimethyl acetal and 70 g (1 mol) of crotonaldehyde are added. The mixture is allowed to stand overnight at room temperature, the liquid phase is decanted off from the molecular sieve and cooled to 0° C., and 40 g of sodium borohydride are added in 1 g portions. The mixture is subsequently stirred overnight at room temperature and concentrated, the concentrate is taken up in 500 ml of water, and the potassium carbonate is added until an organic phase separates off. The mixture is extracted using chloroform, and the extract is dried over potassium carbonate, concentrated and distilled.

Yield: 69.5 g (41.5% of theory)
Boiling point: 85° C./12 mbar b) Ethyl N-(2-butene-1-yl)-N-(2,2-dimethoxyethyl)carbamidate 69 g (0.41 mol) of N-(2-butene-1-yl)-N-(2,2-dimethoxyethyl)-amine are dissolved in 200 ml of toluene, 30 ml of 45% strength sodium hydroxide solution are added, and 43 g (0.44 mol) of ethyl chloroformate are added dropwise, with ice-cooling. Stirring is continued for three hours at room temperature, and the aqueous phase is separated off and extracted with 100 ml of toluene. The extract is dried over potassium carbonate, concentrated and distilled.

Yield: 92 g (94% of theory)
Boiling point: 72° C./0.08 mbar 90 g (0.5 mol) of ethyl N-(2,2-dimethoxyethyl)carbamidate are dissolved in 500 ml of toluene, 100 g of pulverulent potassium hydroxide and 1.5 g of triethylbenzylammonium chloride are added, and 80 g (0.6 mol) of crotyl bromide (isomer mixture) are added dropwise. The mixture is stirred overnight at room temperature the salts are dissolved in water, and the aqueous phase is separated off and extracted once using 100 ml of toluene. The extract is dried over potassium carbonate, concentrated and distilled.

Yield: 112 g (96.8% of theory)
Boiling point: 65° C./0.1 mbar c) Ethyl N-(2-butene-1-yl)-N-(2-oxoethyl)-carbamidate 111 g (0.48 mol) of ethyl N-(2-butene-1-yl)-N-(2,2-dimethoxyethyl)-carbamidate together with 50 g of formic acid are refluxed for three hours in 950 ml of water. The mixture is saturated with sodium chloride and extracted three times using 200 ml portions of methylene chloride. The organic phases are washed to neutrality using sodium hydrogen carbonate solution, dried over magnesium sulphate, concentrated and distilled.

Yield: 77 g (86.6% of theory)
Boiling point: 94 to 100° C./0.15 mbar d) Ethyl 2-benzyl-4-methyl-2,7-diazabicyclo[3.3.0]octane-7-carboxylate

On a water separator, 18.5 g (0.1 mol) of ethyl N-(2-butene-1-yl)-N-(2-oxoethyl)-carbamidate together with 16.5 g (0.1 mol) of N-benzylglycine are refluxed overnight in 300 ml of toluene. The mixture is concentrated and distilled.

Yield: 10 g (25% of theory)
Boiling point: 135 to 142° C./0.1 mbar
Gas chromatography reveals that the product is 76% pure.

e) 2-Benzyl-4-methyl-2,7-diazabicyclo[3.3.0]octane 10 g (26.3 mmol) of ethyl 2-benzyl-4-methyl-2,7-diazabicyclo[3.3.0]octane-7-carboxylate are refluxed overnight together with 100 ml of concentrated hydrochloric acid. The mixture is concentrated, the concentrate is taken up in 20 ml of water, the mixture is rendered alkaline using potassium carbonate and extracted five times using 50 ml portions of chloroform, and the extracts are dried over potassium carbonate, concentrated and distilled.

Yield: 4.6 g (81% of theory)
Boiling point: 87 to 95° C./0.13 mbar
Gas chromatography reveals that the product is 76% pure.

f) 4-Methyl-2,7-diazabicyclo[3.3.0]octane 4.1 g (19 mmol) of 2-benzyl-4-methyl-2,7-diazabicyclo[3.3.0]octane in 80 ml of methanol are hydrogenated on 1 g of palladium/active carbon (10% Pd) at 100° C. and 100 bar. The catalyst is filtered off, the filtrate is concentrated, and the residue is distilled.

Yield: 1.2 g (50% of theory)
Boiling point: 76° C./8 mbar

Example V

5-Fluoromethyl-2-methyl-2,7-diazabicyclo[3.3.0]octane

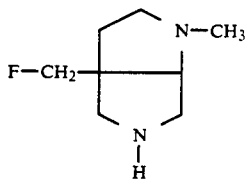

a) Ethyl N-(2-fluoromethylallyl)-N-(2,2-dimethoxyethyl)-carbamidate 8 g (0.26 mol) of sodium hydride (80%) are initially introduced into 200 ml of toluene, 35.8 g (0.2 mol) of ethyl N-(2,2-dimethoxyethyl)-carbamidate are added dropwise at 90° C. The mixture is subsequently stirred for one hour at 90° C., and 32.6 g (0.3 mol) of 1-chloro-2-fluoromethylprop-2-ene are then added dropwise. The mixture is stirred overnight at 90° C., salts are dissolved in water, and the aqueous phase is separated off and extracted with toluene. The organic phases are dried over potassium carbonate, concentrated and distilled.

Yield: 28.2 g (56.6% of theory)
Boiling point: 71 to 79° C./0.07 mbar b) Ethyl N-(2-fluoromethylallyl)-N-(2-oxoethyl)-carbamidate 25 g (0.1 mol) of ethyl N-(2-fluoromethylallyl)-N-(2,2-dimethoxyethyl)-carbamidate together with 5 g of formic acid are refluxed for two hours in 100 ml of water. The mixture is saturated with sodium chloride and extracted with methylene chloride, and the organic phases are washed to neutrality using sodium hydrogen carbonate solution. The organic phases are dried over magnesium sulphate, concentrated and distilled.

Yield: 18.5 g (87% of theory)
Boiling point: 84° C./0.18 mbar c) Ethyl 5-fluoromethyl-2-methyl-2,7-diazabicyclo[3.3.0]octane-7-carboxylate On a water separator, 9.1 g (43 mmol) of ethyl N-(2-fluoromethylallyl)-N-(2-oxoethyl)-carbamidate together with 3.9 g (43 mmol) of pulverulent sarcosine are refluxed overnight in 170 ml of toluene. The mixture is concentrated, and the residue is distilled.

Yield: 7.5 g (75.8% of theory)
Boiling point: 80 to 100° C./0.25 to 0.35 mbar d) 5-Fluoromethyl-2-methyl-2,7-diazabicyclo[3.3.0]octane 7.1 g (26 mmol) of ethyl 5-fluoromethyl-2-methyl-2,7-diazabicyclo[3.3.0]octane-7-carboxylate in 100 ml of concentrated hydrochloric acid are refluxed overnight. The mixture is concentrated, the concentrate is taken up in 20 ml of water, this mixture is rendered alkaline using potassium carbonate and extracted ten times using 50 ml portions of chloroform, and the extracts are dried over potassium carbonate, concentrated and distilled.

Yield: 0.8 g (20% of theory)
Boiling point: 34° C./0.07 mbar

Example W

5-Fluoro-7-methyl-2,7-diazabicyclo[3.3.0]octane

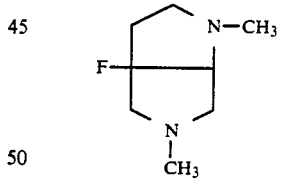

a) Ethyl N-(2,2-dimethoxyethyl)-N-(2-fluoroallyl)-carbamidate 11.6 g (65.5 mmol) of ethyl N-(2,2-dimethoxyethyl)-carbamidate, 15 g of pulverulent potassium hydroxide and 0.25 g of triethylbenzylammonium chloride are initially introduced into 65 ml of toluene, and 10 g (72 mmol) of 2-fluoroallyl bromide are added dropwise at room temperature. The mixture is stirred overnight at room temperature, 100 ml of water are added, and the aqueous phase is separated off and extracted with 30 ml of toluene. The organic solutions are dried over magnesium sulphate and concentrated, and the residue is distilled.

Yield: 14.1 g (91.5% of theory)
Boiling point: 72° C./0.3 mbar b) Ethyl N-(2-fluoroallyl)-N-(2-oxoethyl)-carbamidate 14.1 g (60 mmol) of ethyl N-(2,2-dimethoxyethyl)-N-(2-fluoroallyl)-carbamidate together with 6.3 ml of formic acid are refluxed for three hours in 120 ml of water. The solution is saturated with sodium chloride and extracted several times using methylene chlorides, the organic solutions are washed with saturated sodium hydrogen carbonate solution, dried over magnesium sulphate and concentrated, and the residue is distilled.

Yield: 9.8 g (86% of theory)
Boiling point: 80° C./0.25 mbar c) Ethyl 2-benzyl-5-fluoro-2,7-diazabicyclo[3.3.0]octane-7-carboxylate 20.8 g (0.11 mol) of ethyl N-(2-fluoroallyl)-N-(2-oxoethyl)-carbamidate together with 19 g (0.115 mol) of N-benzylglycine are refluxed in 300 ml of toluene until the evolution of CO$_2$ has ceased. The mixture is concentrated and distilled.

Yield: 16.4 g (44.8% of theory)
Boiling point: 148°-152° C./0.1 mbar

Gas chromatography reveals that the product is 88% pure.

d) 2-Benzyl-5-fluoro-7-methyl-2,7-diazabicyclo[3.3.0]octane

A solution of 16.4 g (49.4 mmol, 88%) of ethyl 2-benzyl-5-fluoro-2,7-diazabicyclo[3.3.0]octane-7-carboxylate in 25 ml of absolute tetrahydrofuran is added dropwise to 4.3 g (0.11 mol) of lithium aluminum hydride in 125 ml of absolute tetrahydrofuran, and the mixture is subsequently refluxed overnight. The mixture is decomposed in succession with in each case 4.5 ml of water, 15% strength potassium hydroxide solution and water, and the inorganic salts are filtered off with suction and extracted three times by boiling with 50 ml portions of tetrahydrofuran. The organic solutions are concentrated, and the residue is distilled.

Yield: 11 g (88% of theory)
Boiling point: 98°-108° C./0.08 mbar

Gas chromatography reveals that the product is 93% pure.

e) 5-Fluoro-7-methyl-2,7-diazabicyclo[3.3.0]octane 11 g (43.7 mmol, 93%) of 2-benzyl-5-fluoro-7-methyl-2,7-diazabicyclo[3.3.0]octane in 100 ml of ethanol are hydrogenated on 2 g of palladium/active carbon (10% Pd) at 100° C. and 100 bar. The catalyst is filtered off with suction, the filtrate is concentrated, and the residue is distilled.

Yield: 4.4 g (69.8% of theory)
Boiling point: 85°-90° C./25 mbar

Example X

Ethyl 6-methyl-2,7-diazabicyclo[3.3.0]octane-7-carboxylate

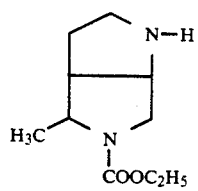

a) Ethyl N-(1-buten-3-yl)-N-(2,2-dimethoxyethyl)-carbamidate 22 g (0.24 mol) of 3-chloro-1-butene are added to 35.5 g (0.2 mol) of ethyl N-(2,2-dimethoxyethyl)carbamidate and 26 g of pulverulent potassium hydroxide in 400 ml of dimethylformamide, and the mixture is heated overnight to 40° C. The salts are dissolved in water, and the mixture is extracted several times using methylene chloride. The organic extracts are dried over potassium carbonate, concentrated and distilled.

Yield: 28.5 g (61.6% of theory)
Boiling point: 60° C./0.08 mbar

Ethyl N-(1-buten-3-yl)-N-(2-oxoethyl)-carbamidate 28.3 g (0.122 mol) of ethyl N-(1-buten-3-yl)-N-(2,2-dimethoxyethyl)-carbamidate together with 65 ml of formic acid are heated for one hour to 100° C. The mixture is poured onto 200 g of ice and extracted with methylene chloride, and the organic extracts are washed with saturated sodium hydrogen carbonate solution, dried over magnesium sulphate, concentrated and distilled.

Yield: 11.6 g (51.3% of theory)
Boiling point: 62°-65° C./0.03 mbar c) Ethyl 2-benzyl-6-methyl-2,7-diazabicyclo[3.3.0]octane-7-carboxylate On a water separator, 11.6 g (62.6 mmol) of ethyl N-(1-buten-3-yl)-N-(2-oxoethyl)-carbamidate and 10.4 g (62.6 mmol) of N-benzylglycine are refluxed overnight in 170 ml of toluene. The mixture is concentrated and distilled.

Yield: 13.7 g (75.9% of theory)
Boiling point: 140°-153° C./0.1 mbar d) Ethyl 6-methyl-2,7-diazabicyclo[3.3.0]octane-7-carboxylate 13 g (44.9 mmol) of ethyl 2-benzyl-6-methyl-2,7-diazabicyclo[3.3.0]octane-7-carboxylate in 150 ml of ethanol are hydrogenated on 2 g of palladium/active carbon (10% Pd) at 100° C. and 100 bar. The catalyst is filtered off, and the filtrate is concentrated and distilled.

Yield: 6.8 g (76.4% of theory)
Boiling point: 81° C./0.09 mbar

Example Y

Diethyl 2,7-diazabicyclo[3.3.0]octane-3,7-dicarboxylate

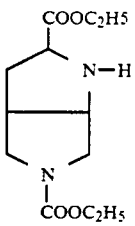

a) Diethyl 2-benzyl-2,7-diazabicyclo [3.3 0]octane-3,7-dicarboxylate

On a water separator, 50 g (0.25 mol) of ethyl N-benzylglycinate in 1 l of toluene are refluxed, and 43 g (0.25 mol) of ethyl N-allyl-N-(2-oxoethyl)-carbamidate are added dropwise in the course of two hours. The mixture is refluxed until water is no longer separated off, concentrated, and the residue is distilled.

Yield: 82.1 g (94.8% of theory)
Boiling point: 160°–165° C./0.05 mbar b) Diethyl 2,7-diazabicyclo[3.3.0]octane-3,7-dicarboxylate 96.5 g (0.279 mol) of diethyl 2-benzyl-2,7-diazabicyclo[3.3.0]octane-3,7-dicarboxylate in 1 l of ethanol are hydrogenated on 5 g of palladium/active carbon (10% Pd) at 100° C. and 100 bar. The liquid phase is filtered off with suction, concentrated and distilled.

Yield: 63.3 g (84.6% of theory)
Boiling point: 137°–140° C./0.18–0.2 mbar

Example Z

Tert.-butyl 5-methyl-2,7-diazabicyclo[3.3.0]octane-7-carboxylate

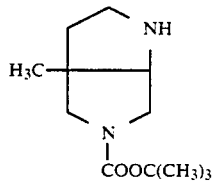

a) Tert.=butyl N-(2-hydroxyethyl)-N-methallylcarbamidate 34.5 g (0.3 mol) of N-methallylethanolamine and 46.2 ml (0.33 mol) of triethylamine are initially introduced into 300 ml of toluene, and 71.2 g (0.32 mol) of tert.-butyl pyrocarbonate are added dropwise. The mixture is stirred overnight at room temperature, washed with saturated sodium chloride solution, dried over potassium carbonate, concentrated and distilled.

Yield: 57.1 g (83% of theory)
Boiling point: 93° C./0.25 mbar
Gas chromatography reveals that the product is 94% pure.

b) Tert.-butyl N-methallyl-N-(2-oxoethyl)-carbamidate 49.4 ml (0.59 ml) of oxalyl chloride are initially introduced into 480 ml of absolute methylene chloride, and 83.3 g (1.07 mol) of dimethyl sulphoxide in 120 ml of absolute methylene chloride are added dropwise at −60° C. 56.6 g (0.25 mol) of tert.-butyl N-(2-hydroxyethyl)-N-methallylcarbamidate in 120 ml of absolute methylene chloride are subsequently added dropwise at −30° C. 169 ml (1.23 mol) of triethylamine are then added dropwise, also at −30° C. The mixture is allowed to come to room temperature and is poured into 1.2 l of ice-water, the organic phase is separated off, and the aqueous phase is extracted with methylene chloride. The organic solutions are washed with sodium chloride solution, dried over magnesium sulphate, concentrated and distilled.

Yield: 38.9 g (71% of theory)
Boiling point: 75° C./0.18 mbar c) Tert.-butyl 2-benzyl-5-methyl-2,7-diazabicyclo[3.3.0]octane-7-carboxylate 10.9 g (50 mmol) of tert.-butyl N-methallyl-N-(2-oxoethyl)-carbamidate and 8.3 g (50 mmol) of N-benzylglycine in 150 ml of toluene are refluxed for 15 hours on a water separator. The mixture is concentrated and distilled.

Yield: 7.2 g (36% of theory)
Boiling point: 142° C./0.35 mbar
Gas chromatography reveals that the product is 80% pure d) Tert.-butyl 5-methyl-2,7-diazabicyclo[3.3.0]octane-7-carboxylate 2.6 9 (10.3 mmol) of tert.-butyl 2-benzyl-5-methyl-2,7-diazabicyclo[3.3.0]octane-7-carboxylate in50 ml of ethanol are hydrogenated on 0.5 g of palladium/active carbon (10% Pd) at 130° C. and 100 bar. The catalyst is filtered off with suction, and the liquid phase is concentrated and distilled.

Yield: 0.9 g (38.6% of theory)
Boiling point: 76° C./0.07 mbar

Example ZA

5-Bromo-2-methyl-2,7-diazabicyclo[3.3.0]octane

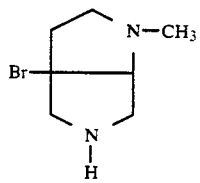

a) Ethyl N-(2-bromoallyl)-N-(2,2-dimethoxyethyl)-carbamidate 88.5 g (0.5 mol) of ethyl N-(2,2-dimethoxyethyl)-carbamidate, 83 g of pulverulent potassium hydroxide and 2 g of triethylbenzylammonium chloride are initially introduced into 500 ml of toluene, and 110 g (0.55 mol) of 2,3-dibromopropene are added dropwise. The mixture is stirred overnight at room temperature, the salts are filtered off with suction, and the filtrate is washed with saturated sodium chloride solution, dried over magnesium sulphate, concentrated and distilled over a Vigreux column.

Yield: 53.7 g (36% of theory)
Boiling point: 70° C./0.07 mbar b) Ethyl N-(2-bromoallyl)-N-(2-oxoethyl)-carbamidate 54 g (0.18 mol) of ethyl N-(2-bromoallyl)-N-(2,2-dimethoxyethyl)-carbamidate together with 20 ml of formic acid are refluxed for three hours in 400 ml of water. The mixture is saturated with sodium chloride, and the aqueous phase is separated off and extracted twice using 150 ml portions of methylene chloride. The organic solutions are washed to neutrality using saturated sodium hydrogen carbonate solution, dried over magnesium sulphate, concentrated and distilled.

Yield: 38.9 g (84.4% of theory)
Boiling point: 106°-109° C./0.25 mbar c) Ethyl 5-bromo-2-methyl-2,7-diazabicyclo[3.3.0]octane-7-carboxylate On a water separator, 25 g (0.1 mol) of ethyl N-(2-bromoallyl)-N-(2-oxoethyl)-carbamidate together with 9 g (0.1 mol) of sarcosine are refluxed overnight in 400 ml of toluene. The mixture is concentrated, and the residue is distilled.

Yield: 19.4 g (64% of theory)
Boiling point: 95°-96° C./0.04 mbar

Gas chromatography reveals that the product is 91.4% pure.

d) 5-Bromo-2-methyl-2,7-diazabicyclo[3.3.0]octane 18.4 g (60.7 mmol, 91.4%) of ethyl 5-bromo-2-methyl-2,7-diazabicyclo[3.3.0]octane-7-carboxylate are refluxed overnight together with 120 ml of concentrated hydrochloric acid. The mixture is concentrated, the concentrate is taken up in 50 ml of water, this mixture is rendered alkaline using potassium carbonate and extracted five times using 100 ml portions of chloroform. The extracts are dried over potassium carbonate, concentrated and distilled.

Yield: 7.2 g (54% of theory)
Boiling point: 90° C./4 mbar

Example ZB

Ethyl 2,7-diazabicyclo[3.3.0]octane-7-carboxylate

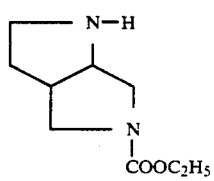

21.2 g (77.3 mmol) of ethyl 2-benzyl-2,7-diazabicyclo[3.3.0]octane-7-carboxylate (Example Ae) in 400 ml of ethanol are hydrogenated on 3 g of palladium/active carbon (10% Pd) at 100° C. and 100 bar. The catalyst is filtered off, the filtrate is concentrated, and the residue is distilled.

Yield: 10.3 g (72.3% of theory)
Boiling point: 82°-92° C./0.1 mbar

Example 1

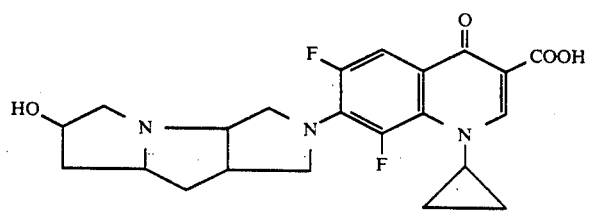

A. 2.85 g (10 mmol) of 1-cyclopropyl-6,7,8-trifluoro-1,4-dihydro-4-oxo-3-quinoline carboxylic acid are refluxed for 3 hours in a mixture of 30 ml of acetonitrile and 15 ml of dimethylformamide in the presence of 1.9 g (17 mmol) of 1,4-diazabicyclo[2.2.2]octane with 2.0 g (12 mmol) of 10-hydroxy-1,4-diazatricyclo[6.3.0.0$^{2,6}$]undecane. The mixture is concentrated, the residue is stirred with water, and the undissolved precipitate is filtered off with suction, washed with water and dried.

Yield: 3.1 g (72% of theory) of 1-cyclopropyl-6,8-difluoro-1,4-dihydro-7-(10-hydroxy-1,4-diazatricyclo[6.3.0.0$^{2,6}$]undec-4-yl)-4-oxo-3-quinolinecarboxylic acid, melting point: 242°-245° C. (with decomposition).

B. 3 g (7 mmol) of the betain of step A are dissolved in 20 ml of 1N hydrochloric acid with heating, the solution is filtered and evaporated, and the residue is stirred with ethanol. The salt obtained is filtered off with suction, washed with ethanol and dried at 120° C./12 mbar.

Yield: 3.1 g (95% of theory) of 1-cyclopropyl-6,8-difluoro-1,4-dihydro-7-(10-hydroxy-1,4-diazatricyclo[6.3.0.0$^{2,6}$]undec-4-yl)-4-oxo-3-quinolinecarboxylic acid hydrochloride, melting point: 267°-275° C. (with decomposition).

| $C_{22}H_{23}F_2N_3O_4 \times HCl$ (467.5) | | | |
| --- | --- | --- | --- |
| Calculated: C 56.47 | H 5.13 | N 8.98 | Cl 7.59 |
| Found: C 56.3 | H 5.3 | N 8.9 | Cl 7.6 |

The following are prepared in accordance with Example 1:

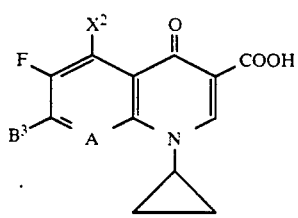
| Example | B³ | X² | A | Melting point[1] (°C. with decomposition) |
|---|---|---|---|---|
| 2A | (pyrrolizidine-CH₂-N—) | H | CF | 225–228 (from GME) |
| 2B | HCl × (pyrrolizidine-CH₂-N—) | H | CF | 287–290 |
| 3 | S-(pyrrolizidine-CH₂-N—) | H | CF | 245–247 (from GME) |
| 4 | S-(pyrrolizidine-CH₂-N—) | H | CCl | 210–212 (from GME/DMF) |
| 5 | CH₃, CH₃, S-(pyrrolizidine-CH₂-N—) | H | CF | 218–220 (from GME) |
| 6 | (bicyclic N—) | H | CF | 199 (sintering) −206 (from GME) |
| 7 | (bicyclic N—) | CH₃ | CH | 178–181 |
| 8 | (bicyclic N—) | H | N | ab 247 |
| 9 | (bicyclic N—) | H | CF | 176–183 (from GME) |

-continued

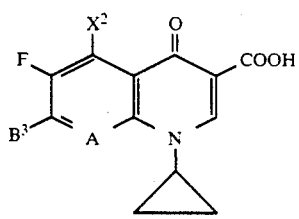

| Example | B³ | X² | A | Melting point[1] (°C. with decomposition) |
|---|---|---|---|---|
| 10 | (piperidine-pyrrolidine bicyclic with N—) | CH₃ | CH | 174–176 |
| 11 | (N-CH₃ pyrrolidine fused with Cl-substituted pyrrolidine, N—) | H | CF | ab 245 (from GME) |
| 12 | (dimethyl N-CH₃ pyrrolidine fused with Cl-substituted pyrrolidine, N—) | H | CF | 236–239 (from GME) |
| 13 | (N-CH₃ pyrrolidine fused with Br-substituted pyrrolidine, N—) | H | CF | 220–223 (from GME) |
| 14 | (bicyclic diazabicycle with N— and N-CH₃) | H | CF | 204–205 (from GME) |
| 15 | (bicyclic diazabicycle with N— and N-CH₃) | H | CH | 188–199 (from GME) |
| 16 | (bicyclic diazabicycle with N— and N-CH₃) | H | C—Cl | 180–182 (from GME) |

-continued

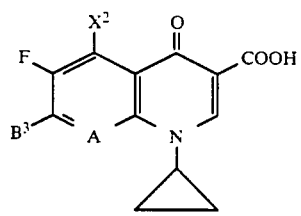

| Example | B³ | X² | A | Melting point[1]) (°C. with decomposition) |
|---|---|---|---|---|
| 17 | 1,8-dimethyl-octahydropyrrolo[3,4-b]pyridine (N-linked), with N-CH₃ | H | CH | 171–175 (from GME) |
| 18 | 4-fluoro-1-methyl-1,4-diazabicycle (piperidine with 4-F, N'-CH₃) | H | CF | 225–227 (from GME) |
| 19 | 4-(fluoromethyl)-1-methyl-piperidine-type, N'-CH₃ | H | CF | 238–242 (from GME) |
| 20 | 4-methyl-piperidine, N'-CO-O-C(CH₃)₃ | H | CF | 213–216 |
| 21 | 4-chloro-piperidine, N'-CO₂C₂H₅ | H | CF | 161–163 |
| 22 | 4-(fluoromethyl)-piperidine, N'-CO₂C₂H₅ | H | CF | 210–212 |

-continued

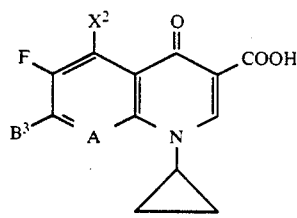

| Example | B³ | X² | A | Melting point[1] (°C. with decomposition) |
|---|---|---|---|---|
| 23 | (N-bicyclic with N-CO₂C₂H₅ and CH₃) | H | CF | 151–152 (from GME) |
| 24 | (N-bicyclic with CH₃ and N-CO₂C₂H₅) | H | CF | 175–177 (from GME) |

[1]The following were used for recrystallisation:
DMF = dimethylformamide
GME = glycol monomethyl ether

Example 25

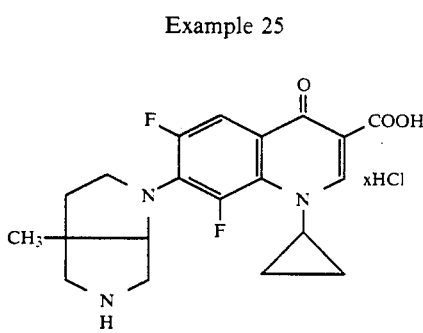

260 mg (0.53 mmol) of 7-(7-tert.-butoxycarbonyl-5-methyl-2,7-diazabicyclo[3.3.0]oct-2-yl)-1-cyclopropyl-6,8-difluoro-1,4-dihydro-4-oxo-3-quinolinecarboxylic acid (from Example 20) are heated for approximately 10 minutes at 80° C. in a mixture of 1.5 ml of methanol and 2.5 ml of concentrated hydrochloric acid. The clear solution is concentrated, the residue is stirred with ethanol, and the precipitate is filtered off with suction, washed with ethanol and dried at 80°/1 mbar.

Yield: 150 mg (66.5% of theory) of 1-cyclopropyl-6,8-difluoro-1,4-dihydro-7-(5-methyl-2,7-diazabicyclo[3.3.0]oct-2-yl)-4-oxo-3-quinolinecarboxylic acid hydrochloride, melting point: 278°–279° C. (with decomposition).

Example 26

3 g (6.3 mmol) of 1-cyclopropyl-7-(7-ethoxycarbonyl-5-fluoromethyl2,7-diazabicyclo[3.3.0]oct-2-yl)-6,8-difluoro-1,4-dihydro-4-oxo-3-quinolinecarboxylic acid (from Example 22) are refluxed for 8 hours in 60 ml of concentrated hydrochloric acid. The suspension is concentrated, and the residue is stirred with ethanol, filtered off with suction, washed with ethanol and dried at 100° C./12 mbar.

Yield: 1.7 g (61% of theory) of 1-cyclopropyl-6,8-difluoro-7-(5-fluoromethyl-2,7-diazabicyclo[3.3.0]oct-2-yl)-1,4-dihydro-4-oxo-3-quinolinecarboxylic acid hydrochloride, melting point: 253°–261° C. (with decomposition); after recrystallisation from glycol monomethyl ether: melting point: 263°–267° C. (with decomposition).

The following ar prepared analogously to Example 26:

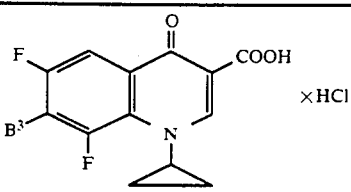

| Example | $B^3$ | Melting point (°C. with decomposition) |
|---|---|---|
| 27 | (structure) | 263–269 |
| 28 | (structure) | 310–315 |
| 28 | (structure) | 297–300 |

Example 29

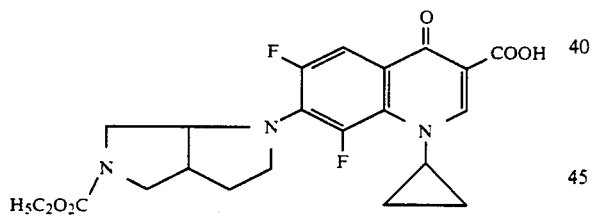

Analogously to Example 1, the reaction is carried out with ethyl 2,7-diazabicyclo[3.3.0]octane-7-carboxylate to give 1-cyclopropyl-7-(7-ethoxycarbonyl-2,7-diazabicyclo[3.3.0]oct-2-yl)-6,8-difluoro-1,4-dihydro-4-oxo-3-quinolinecarboxylic acid of melting point 192°–193° C.

Example 30

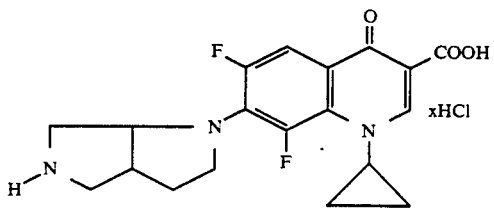

2.5 g of the product from Example 29 are refluxed for 17 hours in 50 ml of concentrated hydrochloric acid. The solution is concentrated, the residue is treated with ethanol, and the undissolved solid product is filtered off with suction, washed with ethanol and dried in vacuo at 100° C.

Yield: 1.3 g of 1-cyclopropyl-7-(2,7-diazabicyclo[3.3.0]oct-2-yl)-6,8-difluoro-1,4-dihydro-4-oxo-3-quinolinecarboxylic acid hydrochloride, melting point: 275°–278° C. (with decomposition); mass spectrum: m/e 375 (M+), 332 (100%, M+—43), 331 (M+—CO$_2$), 315, 289, 274.

We claim:

1. 7-(2,7-Diazabicyclo[3.3.0]octyl-3-quinolonecarboxylic acid derivatives of the formula

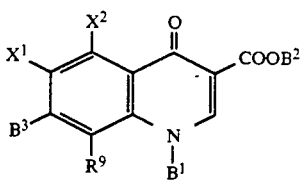

in which $X^1$ represents halogen, $X^2$ represents hydrogen, amino, alkylamino having 1 to 4 carbon atoms, dialkylamino having 1 to 3 carbon atoms per alkyl group, hydroxyl, alkoxy having 1 to 4 carbon atoms, mercapto, alkylthio having 1 to 4 carbon atoms, arylthio, halogen or methyl, $B^1$ represents alkyl having 1 to 4 carbon atoms, alkenyl having 2 to 4 carbon atoms, cycloalkyl having 3 to 6 carbon atoms, 2-hydroxyethyl, 2-fluoroethyl, methoxy, amino, methylamino, ethylamino, dimethylamino, or phenyl which is optionally substituted by 1 or 2 fluorine atoms, $B^2$ represents hydrogen, alkyl having 1 to 4 carbon atoms or (5-methyl-2-oxo-1,3-dioxol-4-yl)-methyl, $B^3$ represents a radical of the structure

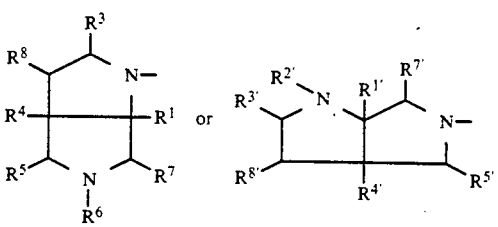

where $R^1$, $R^3$, $R^4$, $R^5$, $R^7$ and $R^8$ are identical or different and in each case represent hydrogen or methyl which can optionally be substituted by halogen or hydroxyl, or represent $C_1$–$C_3$-alkoxycarbonyl or carboxyl, $R^4$ and $R^8$ can additionally represent halogen, amino, hydroxyl or methoxy, $R^6$ represents hydrogen, $C_1$–$C_6$-alkyl, benzyl, $C_6$–$C_{12}$-aryl, $C_1$–$C_3$-alkanoyl, benzoyl or $C_1$–$C_5$-alkoxycarbonyl, $R^{1'}$, $R^{2'}$, $R^{3'}$, $R^{5'}$, $R^{7'}$ and $R^{8'}$ are identical or different and in each case represent hydrogen or methyl, $R^{4'}$ represents halogen, amino, hydroxyl, methoxy or methyl which can optionally be substituted by halogen, amino, hydroxyl or methoxy, or represents hydrogen when R²' and R³' together denote a C₂-C₄-alkylene bridge or a CH₂—S—CH₂ bridge which can optionally be monosubstituted or disubstituted by hydroxyl, methoxy, amino or methyl, R⁹ represents H, halogen, methyl, cyano, nitro, hydroxyl or methoxy, and their hydrates and acid addition salts which can be used in pharmaceuticals, as well as their alkali metal salts, alkaline earth metal salts, silver salts and guanidinium salts.

2. Compounds according to claim 1, in which

X¹ represents fluorine or chlorine,

X² represents hydrogen, amino, alkylamino having 1 to 2 carbon atoms, dimethylamino, hydroxyl, methoxy, mercapto, methylthio, fluorine or methyl, B¹ represents alkyl having 1 to 3 carbon atoms, alkenyl having 2 to 3 carbon atoms, cycloalkyl having 3 to 5 carbon atoms, 2-hydroxyethyl, 2-fluoroethyl, methoxy, amino, methylamino, ethylamino, dimethylamino, or phenyl which is optionally substituted by 1 or 2 fluorine atoms, B² represents hydrogen, alkyl having 1 to 3 carbon atoms or (5-methyl-2-oxo-1,3-dioxol-4-yl)-methyl, R¹, R³, R⁴, R⁵, R⁷ and R⁸ are identical or different and in each case represent hydrogen or methyl which can optionally be substituted by halogen, or represent C₁-C₃-alkoxycarbonyl, R⁴ can additionally represent halogen, R⁶ represents hydrogen, C₁-C₃-alkyl, benzyl, phenyl, acetyl, benzoyl or C₁-C₄-alkoxycarbonyl, R¹', R²', R³', R⁵', R⁷' and R⁸' are identical or different and in each case represent hydrogen or methyl, R⁴' represents halogen, or represents hydrogen when R²' and R³' together denote a C₂-C₄-alkylene bridge or a CH₂—S—CH₂ bridge which can optionally be monosubstituted or disubstituted by hydroxyl or methyl, and their hydrates and acid addition salts which can be used in pharmaceutics, as well as their alkali metal salts and alkaline earth metal salts.

3. Compounds according to claim 1, in which

X¹ represents fluorine,

X² represents hydrogen, amino, fluorine or methyl,

B¹ represents alkyl having 1 to 2 carbon atoms, vinyl, cyclopropyl, 2-hydroxyethyl, 2-fluoroethyl, methoxy, methylamino, 4-fluorophenyl or 2,4-difluorophenyl, B² represents hydrogen or alkyl having 1 to 2 carbon atoms, R¹, R³, R⁴, R⁵, R⁷ and R⁸ are identical or different and in each case represent hydrogen or methyl which can optionally be substituted by fluorine, R⁴ can additionally represent fluorine, chlorine or bromine, R⁶ represents hydrogen, methyl, acetyl or C₁-C₄-alkoxycarbonyl, R¹', R²', R³', R⁵', R⁷' and R⁸' are identical or different and in each case represent hydrogen or methyl, R⁴' represents chlorine or bromine, or represents hydrogen when R²' and R³' together denote a C₂-C₄-alkylene bridge or a CH₂—S—CH₂ bridge which can optionally be monosubstituted or disubstituted by hydroxyl or methyl, and their hydrates and acid addition salts which can be used in pharmaceutics, as well as their alkali metal salts.

4. 1-Cyclopropyl-6,8-difluoro-1,4-dihydro-7-(7-methyl-2,7-diazabicyclo [3.3.0]oct-2-yl)-4-oxo-3-quinolinecarboxylic acid, according to claim 1 of the formula

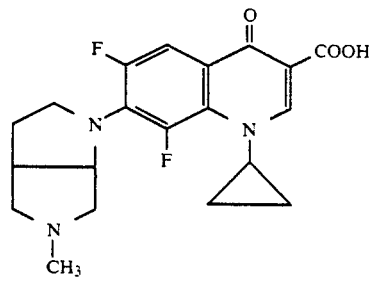

5. 8-Chloro-1-cyclopropyl-6-fluoro-1,4-dihydro-7-(7-methyl-2,7-diazabicyclo [3.3.0]oct-2-yl)-4-oxo-3-quinolinecarboxylic acid according to claim 1, of the formula

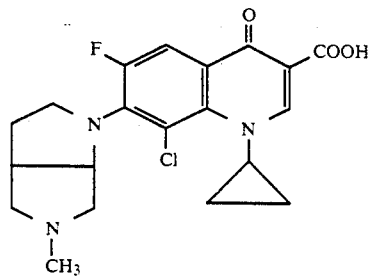

6. 1-Cyclopropyl-6,8-difluoro-1,4-dihydro-7-(5-chloro-2,7-diazabicyclo [3.3.0]oct-2-yl)-4-oxo-3-quinolinecarboxylic acid, according to claim 1 of the formula

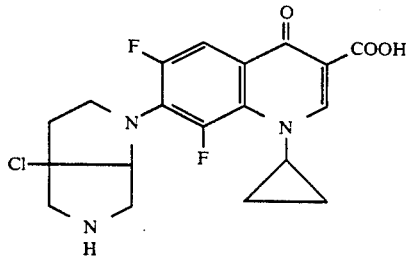

7. 1-Cyclopropyl-7-(1,4-diazatricyclo[6.2.0.0²,⁶]dec-4-yl) -6,8-difluoro-1,4-dihydro-4-oxo-3-quinolinecarboxylic acid according to claim of the formula

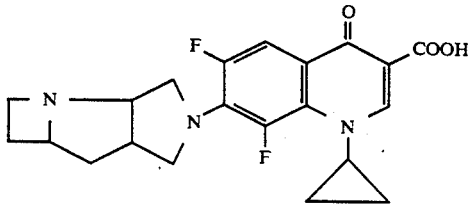

8. 1-Cyclopropyl-7-(2,7-diazabicyclo[3.3.0]oct-2-yl)- 6,8-difluoro-1,4-dihydro -4-oxo-3-quinolinecarboxylic acid according to claim of the formula

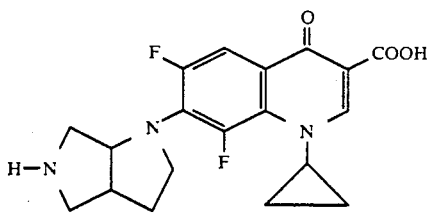

9. An antibiotically active composition comprising an antibiotically effective amount of a compound according to claim 1 and a pharmaceutically acceptable diluent.

10. A method of combatting bacteria in a patient in need thereof which comprises administering to such patient an antibiotically effective amount of a compound according to claim 1, 11. The method according to claim 10, wherein such compound is
1-Cyclopropyl-6,8-difluoro-1,4-dihydro-7-(7-methyl-2,7-diazabicyclo [3.3.0]oct-2-yl)-4-oxo-3-quinolinecarboxylic acid,
8-Chloro-1-cyclopropyl-6-fluoro-1,4-dihydro-7-(7-methyl-2,7-diazabicyclo [3.3.0]oct-2-yl)-4-oxo-3-quinolinecarboxylic acid,
1-Cyclopropyl-6,8-difluoro-1,4-dihydro-7-(5-chloro-2,7-diazabicyclo [3.3.0]oct-2-yl)-4-oxo-3-quinolinecarboxylic acid,
1-Cyclopropyl-7-(1,4-diazatricyclo[6.2.0.0$^{2,6}$]dec-4-yl) -6,8-difluoro-1,4-dihydro-4-oxo-3-quinolinecarboxylic acid or
1-Cyclopropyl-7-(2,7-diazabicyclo[3.3.0]oct-2-yl)-6,8-difluoro -1,4-dihydro-4-oxo-3-quinolinecarboxylic acid.

* * * * *

UNITED STATES PATENT AND TRADEMARK OFFICE
CERTIFICATE OF CORRECTION

PATENT NO. : 5,202,337

DATED : April 13, 1993

INVENTOR(S) : Petersen et al.

It is certified that error appears in the above-identified patent and that said Letters Patent is hereby corrected as shown below:

Col. 58, line 54     After " claim " insert -- 1 --

Col. 58, last line   After " claim " insert -- 1 --

Signed and Sealed this

Twentieth Day of September, 1994

Attest:

BRUCE LEHMAN

Attesting Officer

Commissioner of Patents and Trademarks